US006825018B1

(12) United States Patent
Shibata et al.

(10) Patent No.: US 6,825,018 B1
(45) Date of Patent: Nov. 30, 2004

(54) SORBITOL DEHYDROGENASE, GENE ENCODING THE SAME AND USE THEREOF

(75) Inventors: Takashi Shibata, Tsukuba (JP); Chiyo Ichikawa, Nagoya (JP); Mitsutaka Matsuura, Ichinomiya (JP); Yuji Noguchi, Aichi (JP); Yoshimasa Saito, Mitaka (JP); Michio Yamashita, Tsukuba (JP); Yoko Takata, Osaka (JP)

(73) Assignee: Fujisawa Pharmaceutical Co. Ltd., Osaka (JP)

( * ) Notice: Subject to any disclaimer, the term of this patent is extended or adjusted under 35 U.S.C. 154(b) by 0 days.

(21) Appl. No.: 09/926,163

(22) PCT Filed: Mar. 16, 2000

(86) PCT No.: PCT/JP00/01608

§ 371 (c)(1),
(2), (4) Date: Dec. 21, 2001

(87) PCT Pub. No.: WO00/55329

PCT Pub. Date: Sep. 21, 2000

(30) Foreign Application Priority Data

Mar. 17, 1999 (JP) .......................................... 11-072810
Aug. 6, 1999 (JP) .......................................... 11-224679

(51) Int. Cl.[7] .......................... C12N 9/04; C12N 15/00; C07H 21/04
(52) U.S. Cl. ...................... 435/190; 536/23.2; 435/440
(58) Field of Search ................................ 435/190, 440, 435/183; 536/23.2, 23.1

(56) References Cited

U.S. PATENT DOCUMENTS

| | | | |
|---|---|---|---|
| 5,747,301 A | * | 5/1998 | Hoshino et al. ............ 435/105 |
| 5,753,481 A | | 5/1998 | Niwa et al. |
| 5,834,263 A | | 11/1998 | Niwa et al. |
| 5,861,292 A | | 1/1999 | Niwa et al. |
| 5,888,786 A | | 3/1999 | Niwa et al. |
| 6,197,562 B1 | | 3/2001 | Niwa et al. |

FOREIGN PATENT DOCUMENTS

| | | |
|---|---|---|
| EP | 0 897 984 | 2/1999 |
| EP | 955358 | 11/1999 |
| KR | 98069057 | 10/1998 |
| WO | WO 99/20763 | 4/1999 |

OTHER PUBLICATIONS

T. Shibata, et al., Journal of Bioscience and Bioengineering, vol. 89, No. 5, pp. 463–468, XP–002226528, "Cloning of a Gene for D–Sorbitol Dehydrogenase from Gluconobacter Oxydans G624 and Expression of the Gene in *Pseudomonas putida* IFO3738", May 2000.

Derwent Abstracts, AN–1981–33652D, XP–002226529, JP 56–029994, Mar. 25, 1981.

Osao Adachi, et al., Bioscience Biotechnology Biochemistry, vol. 63, No. 12, pp. 2137–2143, "Crystallization and Properties of NADPH–Dependent L–Sorbose Reductase from Gluconobacter Melanogenus IFO 3294", Dec. 1999.

Young–Min Park, et al., Biotechnology Letters, vol. 16, No. 4, pp. 345–348, "Effect of Toluene–Permeabilization on Oxidation of D–Sorbitol to L–Sorbose by Gluconobacter Suboxydans Cells Immobilized in Calcium Alginate", 1994.

* cited by examiner

*Primary Examiner*—Rebecca E. Prouty
*Assistant Examiner*—Yong D. Pak
(74) *Attorney, Agent, or Firm*—Oblon, Spivak, McClelland, Maier & Neustadt, P.C.

(57) ABSTRACT

A gene encoding D-sorbitol dehydrogenase (SLDH); a process for producing SLDH by culturing host cells transformed by an expression vector having the above gene; and a process for processing L-sorbose or 2-keto-L-gulonic acid (2KLGA) by using the above culture. 2KLGA is an important intermediate in the production of L-ascorbic acid. Thus, a process for producing L-ascorbic acid from the 2KLGA obtained by the above process is also provided.

5 Claims, 7 Drawing Sheets

SORBITOL DEHYDROGENASE, GENE ENCODING THE SAME AND USE THEREOF

TECHNICAL FIELD

This invention relates to a novel sorbitol dehydrogenase (in the present invention, sorbitol dehydrogenase means an enzyme capable of catalyzing a reaction for converting D-sorbitol to L-sorbose by oxidation; hereinafter to be referred to as SLDH), a gene encoding the same, a method for producing L-sorbose and 2-keto-L-gulonic acid (hereinafter to be referred to as 2KLGA) by gene manipulation using said gene, and an expression system involved in the production thereof. The present invention further relates to a method for producing L-ascorbic acid or a salt thereof utilizing the 2KLGA obtained by the above-mentioned method.

BACKGROUND ART

L-sorbose is an important intermediate for the synthesis of L-ascorbic acid (vitamin C) by the Reichstein method (see FIG. 1). When D-sorbitol is chemically oxidized, approximately a half of the product becomes D-sorbose, whereas when D-sorbitol is brought into contact with a microorganism having an SLDH activity, only an L-enantiomer is obtained in a yield of about 95%. Therefore, a fermentation method has been conventionally used for converting D-sorbitol to L-sorbose.

On the other hand, 2KLGA is industrially synthesized by chemically oxidizing L-sorbose. There are known microorganisms that convert L-sorbose into 2KLGA by a two-step enzymatic oxidation reaction by L-sorbose dehydrogenase (SDH) and L-sorbosone dehydrogenase (SNDH), but the production amount of 2KLGA is low by these methods.

As a method by which to produce 2KLGA more efficiently than before by a fermentation method, there is mentioned a method comprising isolating an SLDH gene, introducing the gene into a microorganism having an SDH or SNDH activity to give a recombinant microorganism capable of synthesizing 2KLGA from D-sorbitol, and bringing the microorganism into contact with D-sorbitol.

Several types of SLDHs have been isolated [*Agric. Biol. Chem.*, 46(1), 135–141 (1982); *Biokhimiia*, 43(6), 1067–1078 (1978); J. Biol. Chem., 224, 323 (1957); J. Biol. Chem., 226, 301 (1957); *J. Bacteriol.*, 71, 737 (1956)]. The present inventors have already isolated, from a strain belonging to *Gluconobacter oxydans*, a gene encoding SLDH which is of a membrane-bound type, consists of two large and small subunits and which binds with cytochrome c-like polypeptide and acts (international patent publication No. WO99/20763). However, there is no report on the cloning of a different type of SLDH gene.

It is therefore an object of the present invention to provide a novel SLDH gene useful for the fermentative production of 2KLGA, and to provide a host microorganism transformed with said gene, particularly a transformant obtained by introducing said gene into a host already having SDH and SNDH activity, or a transformant obtained by introducing said gene together with SDH gene and SNDH gene. Another object of the present invention is to provide a method for producing L-sorbose or 2KLGA from D-sorbitol using said microorganism, and to provide a method for producing L-ascorbic acid from 2KLGA obtained by this method. It is yet another object of the present invention to provide a method for producing a recombinant SLDH by culture of a host microorganism transformed with said SLDH gene and a method for producing L-sorbose by an enzyme method using said SLDH.

DISCLOSURE OF THE INVENTION

The present inventors have conducted intensive studies in an attempt to solve the above-mentioned problems and succeeded in cloning a DNA containing a coding region of SLDH from a chromosomal DNA library of a strain belonging to the genus Gluconobacter having said enzyme activity. As a result of the sequencing, the DNA was confirmed to contain a novel SLDH gene completely different from the SLDH gene previously isolated by the present inventors. Moreover, the present inventors transformed Pseudomonas with an expression vector containing the DNA and succeeded in purifying a recombinant SLDH from the culture of said recombinant Pseudomonas. They have also transformed Pseudomonas transformed with an expression vector containing said DNA, with an expression vector containing an SDH gene and an SNDH gene and efficiently converting D-sorbitol to 2KLGA using the culture of this transformant, which resulted in the completion of the present invention.

Accordingly, the present invention provides the following.

(1) An SLDH having the following physicochemical properties:
 (a) action: catalyzes the reaction converting D-sorbitol to L-sorbose
 (b) molecular weight: about 54 kDa
 (c) coenzyme: NAD(P)$^+$ dependent
 (d) substrate specificity: specifically oxidizes sorbitol, mannitol and arabitol, but does not act on xylitol, ribitol, inositol and glycerol.
(2) The SLDH of the above-mentioned (1), which is derived from the strain Gluconobacter oxydans G624.
(3) An SLDH which is originated from the same gene as is the SLDH of the above-mentioned (2) in its molecular evolution.
(4) The SLDH of the above-mentioned (3), which is derived from a bacteria belonging to the genus Gluconobacter.
(5) An SLDH which is the following protein (a) or (b):
 (a) a protein consisting of an amino acid sequence depicted in Sequence Listing SEQ ID NO:2
 (b) a protein consisting of the same amino acid sequence as (a) above, except that one to several amino acids are deleted, substituted, inserted, added or modified, which catalyzes a reaction converting D-sorbitol to L-sorbose.
(6) A DNA encoding the SLDH of any of the above-mentioned (1) to (5).
(7) The DNA of the above-mentioned (6), which is (a) or (b) of the following:
 (a) a DNA having a base sequence of base numbers 537–1991 of the base sequence depicted in Sequence Listing SEQ ID NO:1
 (b) a DNA capable of hybridizing to the base sequence of the above-mentioned (a) under stringent conditions.
(8) The DNA of the above-mentioned (6) or (7), which is derived from bacteria belonging to the genus Gluconobacter.
(9) A gene encoding a protein having an SLDH activity, which is a DNA capable of hybridizing a DNA having a base sequence of base numbers 537–1991 of the base sequence depicted in Sequence Listing SEQ ID NO:1 and a partial DNA thereof.

(10) A protein derived from the genus Gluconobacter, which is encoded by the gene of the above-mentioned (9) and which has an SLDH activity.

(11) A promoter gene comprising the DNA of the following (a) or (b)
  (a) a DNA having a base sequence of base numbers 1–536 of the base sequence depicted in Sequence Listing SEQ ID NO:1
  (b) a DNA having a base sequence of the above-mentioned ~(a) wherein one to several bases is (are) deleted, substituted, inserted, added or modified, which DNA shows a promoter activity at least in one microorganism.

(12) A recombinant vector comprising a DNA of any of the above-mentioned (6) to (9).

(13) An expression vector comprising a DNA of any of the s above-mentioned (6) to (9).

(14) The expression vector of the above-mentioned (13), further comprising a DNA encoding an SDH and/or a DNA encoding an SNDH.

(15) A transformant obtained by transforming a host cell with an expression vector of the above-mentioned (13) or (14).

(16) The transformant of the above-mentioned (15), which belongs to a genus selected from the group consisting of Escherichia coli, the genus Pseudomonas, the genus Gluconobacter, the genus Acetobacter and the genus Pseudogluconobacter.

(17) The transformant of the above-mentioned (15) or (16), which is capable of converting D-sorbitol to 2-KLGA.

(18) A method for producing a protein having an SLDH activity, which method comprises culturing a host cell transformed with an expression vector of the above-mentioned (13) in a medium and harvesting the SLDH of any of the above-mentioned (1) to (5) or the protein of (10) from the obtained culture.

(19) A method for producing an L-sorbose, which method comprises culturing a host cell transformed with an expression vector of the above-mentioned (13) in a medium and bringing D-sorbitol into contact with the obtained culture or a treated product thereof.

(20) A method for producing 2-KLGA, which method comprises culturing a host cell transformed with an expression vector containing a DNA encoding an SDH and a DNA encoding an SNDH in a medium and bringing the L-sorbose obtained according to the method of the above-mentioned (19) into contact with the obtained culture or a treated product thereof.

(21) A method for producing 2-KLGA, which method comprises culturing the transformant of the above-mentioned (17) in a medium and bringing D-sorbitol into contact with the obtained culture or a treated product thereof.

(22) A method for producing L-ascorbic acid or an alkali metal salt thereof or an alkaline earth metal salt thereof, which method comprises converting 2-KLGA obtained by the method of the above-mentioned (20) or (21) to L-ascorbic acid or an alkali metal salt thereof or an alkaline earth metal salt thereof.

The recombinant cell that expresses the SLDH gene of the present invention can be a useful means for the fermentative production of L-sorbose and 2KLGA. Therefore, the present invention is extremely useful for facilitated and large-scale production of L-ascorbic acid.

BEST MODE FOR CARRYING OUT THE INVENTION

Figure 1:
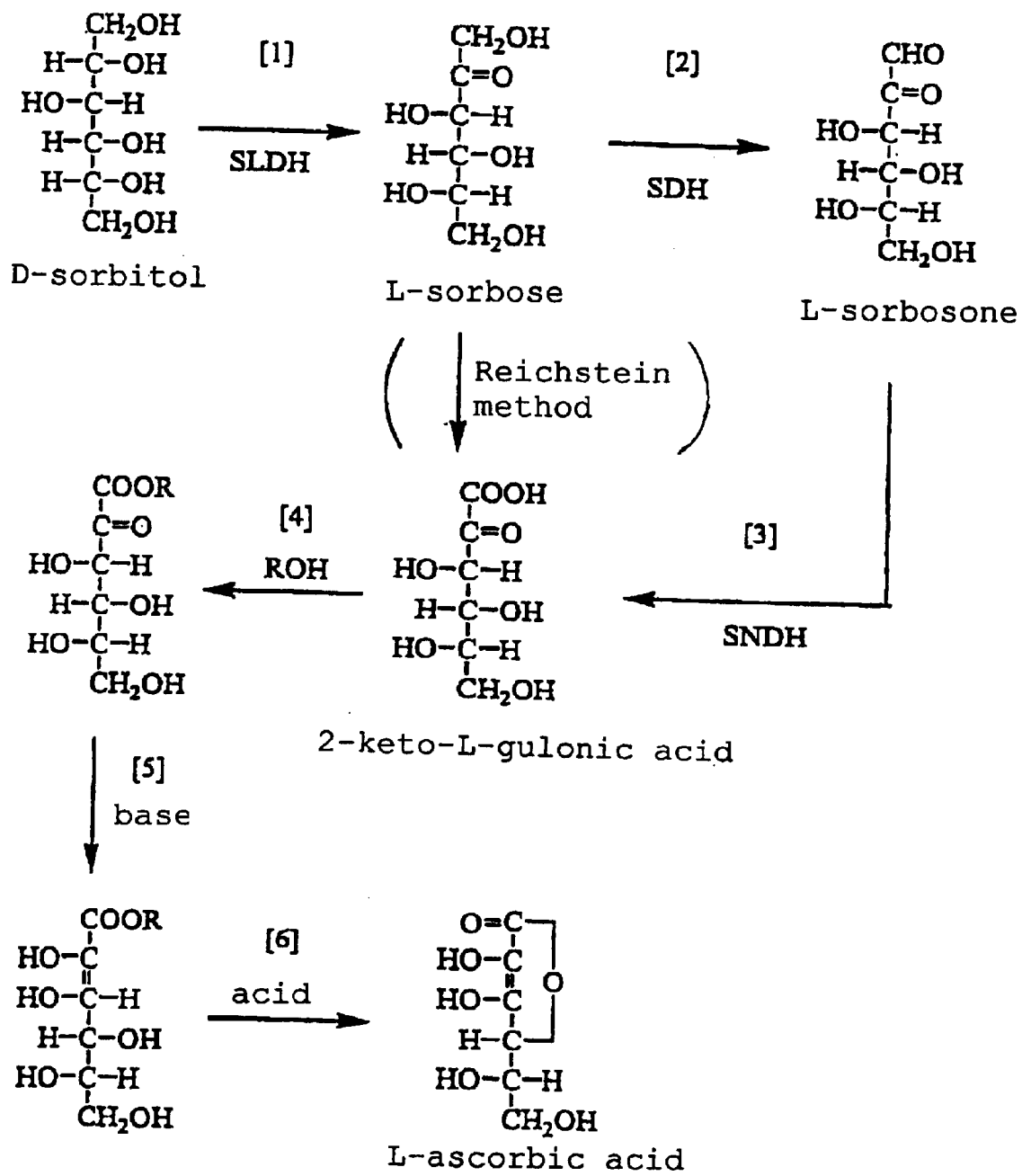
FIG. 1 shows a reaction scheme of the synthesis of L-ascorbic acid, wherein R is alkyl group.

The SLDH of the present invention is a protein having a molecular weight of about 54 kDa, which catalyzes a reaction to convert D-sorbitol to L-sorbose, and characteristically requires $NADP^+$ or $NAD^+$ as a coenzyme. This enzyme can specifically oxidize mannitol and arabitol besides sorbitol, but does not act on xylitol, ribitol, inositol or glycerol.

The SLDH of the present invention is not particularly limited as regards the derivation as long as it shows the above-mentioned characteristics. It may be derived from a naturally occurring organism, a spontaneous or artificial mutant, or a transformant which is obtained by introducing a heterologous (i.e. foreign) SLDH gene. Preferably, SLDH derived from acetic acid bacteria, particularly bacteria belonging to the genus Gluconobacter, more preferably Gluconobacter oxydans, particularly the strain Gluconobacter oxydans 6624 (FERM BP-4415; International Patent Publication No. WO95/23220) are exemplified. In another preferable mode, the SLDH of the present invention is an SLDH derived from the same gene as is the SLDH derived from the strain G. oxydans 6624 in its molecular evolution. As used herein, by the "derived from the same gene . . . in its molecular evolution" is meant an SLDH reasonably concluded to have evolved from the same gene as has an SLDH derived from strain G. oxydans 6624 in its molecular evolution, as a result of the analyses of DNA sequence, physiological role and the like, and their DNA sequences show high homology. These SLDHs preferably have not less than 60%, most preferably not less than 80%, homology in the DNA sequence with an SLDH derived from the strain G. oxydans 6624. These genes can be cloned based on the DNA sequence depicted in Sequence Listing
  SEQ ID NO:1 and using a suitable primer according to the PCR method or using a suitable probe according to the hybridization method, as detailed later.

In a more preferable mode, the SLDH of the present invention is a protein having an amino acid sequence depicted in Sequence Listing SEQ ID NO:2 or a protein having an amino acid sequence having the amino acid sequence comprising one to several amino acids deleted, substituted, inserted, added or modified, as long as the SLDH activity is not impaired.

The SLDH of the present invention can be obtained by appropriately using (1) a method comprising isolating and purifying it from a culture of a cell or tissue as a starting s material that produces the enzyme, (2) a method comprising chemical synthesis, (3) a method comprising purifying it from a cell manipulated by gene recombinant technique to express SLDH and the like.

The isolation and purification of SLDH from a naturally lo occurring SLDH producing cell includes, for example, the following steps. The cell is cultured in a suitable liquid medium, and a fraction having an SLDH activity is separated and recovered from the obtained culture. For example, when the enzyme is localized in cytosol (the SLDH of the present invention being NAD(P)$^+$ dependent, localization in cytosol is expected), the culture is centrifuged and/or filtrated to recover the cell, and the cell is ruptured by ultrasonication, lysozyme treatment, osmotic pressure shock and the like and centrifuged at about 10,000–40,000 rpm to recover a supernatant (soluble fraction). The objective SLDH can be purified from the obtained soluble fraction by appropriately combining separation techniques conventionally used for separation and purification of enzyme proteins. Such separation techniques include, for example, methods utilizing difference in solubility such as salting out, solvent precipitation method and the like, methods utilizing difference in molecular weight such as dialysis, ultrafiltration, gel filtration, non-denatured polyacrylamide gel electrophoresis (PAGE), SDS-PAGE and the like, methods utilizing charge such as ion exchange chromatography, hydroxyl apatite chromatography and the like, methods utilizing specific affinity such as affinity chromatography and the like, methods utilizing hydrophobicity such as reverse-phase high performance liquid chromatography and the like, and methods utilizing difference in isoelectric point such as isoelectric focusing and the like.

Production of the SLDH of the present invention by chemical synthesis includes the steps of, for example, synthesizing, based on the amino acid sequence depicted in Sequence Listing SEQ ID NO:2, the entirety or a part of each sequence using peptide synthesizer, and renaturating the obtained polypeptide under suitable renaturation conditions.

The SLDH derived from *G. oxydans* G624, which is one mode of the present invention, is an extremely unstable enzyme in non-physiological conditions, and may be deactivated during purification by the above-mentioned method. Such enzyme can be quickly purified by affinity chromatography utilizing an added/modified sequence having affinity for a specific substance, according to the histidine tag method, GST method and the like. Therefore, a particularly preferable method for obtaining the SLDH of the present invention includes the steps of, as detailed in the following, cloning a DNA encoding the enzyme from the DNA of a cell having this enzyme, and adding, to this DNA by gene manipulation, a nucleotide sequence encoding an amino acid sequence capable of adsorbing to a metal ion chelate.

An enzyme gene can be generally cloned by the following method. A desired enzyme is purified completely or partially from a cell or tissue that produces the enzyme by the above-mentioned method, and the N terminal amino acid sequence is determined by the Edman method. The enzyme is partially digested by a sequence-specific protease and the amino acid sequence of the obtained oligopeptide is also determined by the Edman method. Oligonucleotides having base sequences corresponding to the amino acid sequences thus determined are synthesized, and using these as primers or probes, a DNA is encoding this enzyme is cloned from RNA or DNA prepared from a cell or tissue capable of producing the enzyme, by the PCR method or colony (or plaque) hybridization method.

Alternatively, an antibody against the enzyme is prepared using the entirety or a part of a completely or partially purified enzyme as an antigen by a conventional method, and a DNA encoding the enzyme can be cloned from a cDNA or genomic DNA library prepared from a cell or tissue capable of producing the enzyme, by immunoscreening.

However, in the case of an enzyme that is unstable and whose purification is difficult, such as the above-mentioned SLDH derived from *G. oxydans* G624, the gene of the enzyme can be screened using its enzyme activity as a marker, as a fragment containing its promoter sequence from the genomic DNA library. Inasmuch as SLDH converts D-sorbitol to L-sorbose, a clone having an SLDH activity can be selected by detecting the generated L-sorbose. Note that the application of this method often accompanies technical difficulty.

To be specific, a chromosomal DNA is isolated from a cell or tissue having an SLDH activity by a conventional method, and digested by a suitable restriction enzyme, lo preferably partially digested by a restriction enzyme having many restriction sites in a chromosomal DNA, and the obtained fragment is inserted in a suitable cloning vector. As the cloning vector, exemplified are plasmid vector, phage vector and the like. Because of the capability of accommodating a large DNA insert and recovering as a colony, a cosmid vector and a charomid vector are preferable. When a phage vector, a cosmid vector and the like are used, in vitro packaging is further applied to obtain a genomic DNA library.

When a cosmid library is used, a suitable indicating bacteria, preferably *Escherichia coli* competent cell having high transformation capability, after infection with a packaging solution obtained as above, is plated on a solid medium and cultured. The resulting respective colonies are individually inoculated to a liquid medium containing D-sorbitol and cultured. After the completion of the culture, a culture supernatant is recovered and candidate clones having an SLDH activity are selected using, for example, a color identification reaction with ketohexose, such as a resorcin-hydrochloric acid reaction (Cohen, *J. Biol. Chem.*, 201, 71, 1953), a resorcin-ferric salt-hydrochloric acid reaction (Kulka, *Biochem. J.*, 63, 542, 1956) and the like.

The presence of SLDH activity (conversion of D-sorbitol to L-sorbose) in the obtained clone is confirmed by the detection of sorbose in the culture supernatant by, for example, HPLC and the like.

Because the DNA insert of cosmid clone is considerably large (35–45 kb), a part of a non-SLDH gene region of the insert DNA is desirably removed for downsizing for facilitated subcloning to plasmid. For downsizing of the DNA insert, for example, subcloning to a charomid vector and the is like is employed. Since a charomid vector has a spacer DNA of various lengths, DNA having various lengths smaller than a cosmid vector can be cloned. In the present invention, for example, a charomid vector capable of accommodating an about 10–20 kb DNA insert is preferably used. The charomid clone having an SLDH activity can be selected according to the method mentioned above.

The subcloning to a plasmid vector can be done by, for example, applying plural charomid clones obtained as mentioned above to restriction enzyme mapping, downsizing a DNA insert using a restriction enzyme found to have no restriction site in the SLDH gene, and ligating with a plasmid vector that underwent a restriction enzyme treatment.

Apart from the above-mentioned strategy, moreover, a DNA encoding the SLDH of the present invention can be directly cloned using the PCR method. That is, PCR is conducted according to a conventional method, using a genomic DNA or cDNA (or mRNA) derived from a cell or tissue having the enzyme activity as a template, and using a pair of oligonucleotides, where an amplification fragment suitably covers the coding region of SLDH, as a primer to amplify a DNA fragment containing the coding region of SLDH. This method is particularly useful for cloning of an SLDH gene having the same origin in the molecular evolution with an SLDH having a known sequence. For example, when an SLDH gene derived from a bacteria, which is speculated to have the same origin in the molecular evolution with an SLDH derived from the strain *G. oxydans* G624, is to be cloned, sense and antisense primers capable of amplifying a DNA fragment having high homology with a DNA fragment containing a base sequence of base number 537–1991 from the sequence is constructed based on the DNA sequence depicted in Sequence Listing SEQ ID NO:2 and the PCR method is performed. When the DNA sequence of SLDH having high homology with the objective SLDH is unknown, for example, PCR is performed using some sequences conserved relatively well in the 5' upstream region as sense primers, and some complementary strand sequences conserved relatively well in the 3' downstream region as antisense primers to clone the SLDH gene. When the upstream and downstream sequences of SLDH are unknown, the annealing temperature needs to be set lower, so that a template DNA and a primer to be used containing some mismatches can still be bound. Therefore, the PCR product may be a mixture of a fragment containing the objective SLDH gene and a non-specific amplification fragment. In this case, the obtained amplification fragment is cloned to a suitable cloning vector (for example, plasmid vector for TA cloning and the like). When the objective amplification fragment does not contain a promoter region, the obtained amplification fragment is cloned to an expression vector, with which a competent cell, such as *Escherichia coli*, is transformed, and the transformant having an SLDH activity is screened by the aforementioned method.

As a different strategy for the cloning of an SLDH gene having the same origin in the molecular evolution with an SLDH having a known sequence, direct cloning by hybridization method such as Southern method and the like may be employed, wherein a genomic DNA or cDNA (or mRNA) derived from a cell or tissue having an SLDH activity is used as a template and the entirety or a part of a known DNA sequence is used as a probe. The conditions of the hybridization may be an appropriately altered stringency depending on the origin of the DNA. For example, the conditions may be changed based on the degree of closeness in the relation of the microorganism to be cloned and the like, such as those under which, of the base sequence, only a sequence having about not less than 60% homology forms a hybrid, only a sequence having about not less than 80% homology forms a hybrid, and the like.

The base sequence of the DNA insert obtained in the above-mentioned manner can be identified by a known sequencing technique, such as Maxam-Gilbert method, dideoxy termination method and the like.

A DNA encoding the SLDH of the present invention preferably encodes an amino acid sequence depicted in v. Sequence Listing SEQ ID NO:2, or an amino acid sequence wherein, in the above-mentioned amino acid sequence, 1 to several amino acids are deleted, substituted, inserted or added (provided that a protein consisting of the mutated amino acid sequence can catalyze the reaction to convert D-sorbitol to L-sorbose). More preferably, a DNA encoding the SLDH of the present invention is a DNA substantially consisting of a base sequence having a base number 537–1991 of the base sequence depicted in Sequence Listing SEQ ID NO:1. As used herein, by the "DNA substantially consisting of" is meant a DNA consisting of this specific base sequence and a DNA consisting of a base sequence capable of hybridizing to the DNA consisting of this specific base sequence under stringent conditions, and encoding a protein having similar physicochemical properties as the protein encoded by the DNA consisting of this specific base sequence.

The "stringent conditions" here mean those under which a DNA having about not less than 60% homology of base sequence can hybridize. The stringency can be controlled by appropriately changing the temperature, salt concentration and the like of hybridization reaction and washing.

The DNA of the present invention may be a DNA obtained from a genomic DNA as mentioned above, or a cDNA obtained from mRNA, or DNA chemically synthesized based on a base sequence having a base number 537–1991 from the base sequence depicted in Sequence Listing SEQ ID NO:1.

The DNA of the present invention may be a DNA obtained from a genomic DNA as mentioned above, or a cDNA obtained from mRNA, or DNA chemically synthesized based on a base sequence having a base number 537–1991 from the base sequence depicted in Sequence Listing SEQ ID NO:1.

The DNA encoding SLDH, which is obtained from a genomic DNA with the SLDH activity as an index as mentioned above, contains a promoter gene sequence in the 5' upstream region. This promoter gene preferably has a base sequence having a base number 1–536 from the base sequence depicted in Sequence Listing SEQ ID NO:1, or said base sequence wherein one to several amino acids are deleted, substituted, inserted, added or modified, which is a DNA having a promoter activity in at least one microorganism. As the "microorganism" here, there are preferably exemplified prokaryotes such as bacteria (e.g., *Escherichia coli, Bacillus subtilis*, Pseudomonas, Gluconobacter, Pseudogluconobacter, Acetobacter and the like) and actinomyces, and certain eucaryotes such as yeast and the like.

The present invention provides a recombinant vector lo containing a DNA encoding the SLDH of the present invention. The recombinant vector of the present invention is not particularly limited as long as it can replicate/maintain or autonomously proliferate in various host cells of procaryotic and/or eucaryotic cells, and encompasses a plasmid vector, a phage vector and the like. The recombinant vector can be conveniently prepared by inserting a DNA encoding SLDH into a cloning vector or expression vector available in the pertinent field, by the use of a suitable restriction enzyme site.

Particularly, the recombinant vector of the present invention is an expression vector wherein a DNA encoding SLDH is disposed under the control of a promoter functional in a certain host cell. Usable vector is not particularly restricted as long as it contains a promoter region functional in various host cells such as procaryotic and/or eucaryotic cells and is capable of controlling the transcription of a gene disposed in the downstream thereof, and a transcription termination signal of said gene, namely, a terminator region, wherein said promoter region and the terminator region are ligated via a sequence containing at least one restriction enzyme recognition site, preferably a unique restriction site. It is preferable that it further contain a selection marker gene for the selection of a transformant. Where desired, this expression vector may contain an initiation codon and a stop codon in the downstream of the promoter region and the upstream of the terminator region, respectively.

When bacteria is used as a host cell, an expression vector generally needs to contain, in addition to the above-mentioned promoter region and terminator region, a replicable unit capable of autonomous replication in a host cell. The promoter region includes a promoter, an operator and a Shine-Dalgarno (SD) sequence. For example, when the host is *Escherichia coli*, trp promoter, lac promoter, recA promoter, lpp promoter, tac promoter and the like are exemplified as the promoter region, and when the host is *Bacillus subtilis*, the promoter region includes SPO1 promoter, SPO2 promoter, penP promoter and the like. As the terminator region, a naturally occurring or synthetic terminator, which is typically used, can be used. As the selection marker gene, resistant genes against various drugs, such as tetracyclin, ampicillin, kanamycin and the like, can be used. As the initiation codon, ATG is generally used. In some cases, GTG can be also used. As the stop codon, conventional TGA, TAA and TAG can be used.

When a DNA encoding the SLDH of the present invention is prepared from a genomic DNA derived from a cell or tissue that produces the enzyme, and obtained in a form containing inherent promoter and terminator regions, and the expression vector of the present invention can be prepared by inserting the DNA into a suitable site of a known cloning vector that can replicate/maintain or autonomously proliferate in a host cell to be transformed. The usable cloning vector in the case where the host is bacteria is exemplified by pBR vector, pUC vector and the like derived from *Escherichia coli*, pUB110, pTP5 and pC194, derived from *Bacillus subtilis*, and the like.

When an expression vector containing a DNA encoding the SLDH of the present invention is used for the production of a recombinant SLDH, particularly when the SLDH is extremely unstable and typical purification method may cause deactivation of the enzyme on the way of purification, the use of an expression vector containing a modified SLDH coding sequence, as in the following, is particularly preferable. The modified SLDH coding sequence comprises, a sequence wherein a base sequence encoding a specific amino acid sequence capable of accelerating the purification of SLDH is added to the terminus of the SLDH coding sequence to allow expression of SLDH in which the specific amino acid sequence has been added to the terminus of the original SLDH amino acid sequence. The specific amino acid sequence capable of accelerating the purification of SLDH is exemplified by amino acid sequence capable of adsorbing to a metal ion chelate, preferably a sequence consisting of basic amino acids such as histidine, lysine, arginine and the like, more preferably a sequence consisting of histidine. Such sequence can be added to the terminus of amino or carboxyl of SLDH, with preference given to addition to the carboxyl terminus. Such modified SLDH coding sequence can be constructed by synthesizing an oligonucleotide wherein a base sequence encoding the amino acid sequence to be added is added to a base sequence consistent with a terminus sequence of the inherent SLDH coding sequence, and, using this as one of the primers and SLDH DNA as a template, performing PCR. The resulting recombinant SLDH can be quickly isolated and purified using a carrier on which a metal ion chelate capable of adsorbing the added amino acid sequence has been immobilized, as detailed in the following.

When an expression vector containing a DNA encoding the SLDH of the present invention is used for the production of 2KLGA, an expression vector containing, in addition to the DNA, a DNA encoding SDH and/or SNDH in a form permitting expression in the host cell may be used. The DNA encoding SLDH, a DNA encoding SDH and a DNA encoding SNDH may be placed under control of different promoters, or two of which or more may be placed in tandem under the control of the same promoter.

The transformant of the present invention can be prepared by transforming a host cell with a recombinant vector containing a DNA encoding the SLDH of the present invention. The host cell is not particularly limited as long as it can be adapted to the recombinant vector to be used and can be transformed, and various cells conventionally used in this field, such as a naturally occurring cell or an artificially produced mutant cell or a recombinant cell, can be utilized. Preferably, bacteria, particularly *Escherichia coli* (e.g., DH5, HB101 and the like), *Bacillus subtilis*, the genus Pseudomonas bacteria (e.g., *Pseudomonas fluorescence* and the like), the genus Gluconobacter bacteria (e.g., *Gluconobacter oxydans* and the like), the genus Pseudogluconobacter bacteria, the genus Acetobacter bacteria and the like are used.

A recombinant vector can be introduced into a host cell 2o by a method conventionally known. For example, when the host is bacteria such as *Escherichia coli, Bacillus subtilis* and the like, the method of Cohen et al. [*Proc. Natl. Acad. Sci. USA*, 69: 2110 (1972)], protoplast method [*Mol. Gen. Genet.*, 168: 111 (1979)], competent method [*J. Mol. Biol.*, 56: 209 (1971)], electroporation method and the like can be used.

Particularly, the transformant of the present invention is a host cell transformed with an expression vector containing a DNA encoding the SLDH of the present invention.

When the transformant is prepared with the aim of producing 2KLGA from D-sorbitol, the host cell needs to have an ability to convert L-sorbose to 2KLGA. Preferably, the host cell produces SDH and SNDH activity. Such naturally occurring cell is, for example, bacteria belonging to the genus Gluconobacter, the genus Acetobacter, the genus Pseudogluconobacter and the like, specifically *Gluconobacter oxydans* T-100 (FERM BP-4415; International Patent Publication No. WO95/23220) and the like. Such artificially prepared cell is, for example, a cell transformed with an expression vector functionally containing a DNA encoding SDH and SNDH isolated from the above-mentioned naturally occurring is bacteria and the like, preferably *Escherichia coli*, the genus Pseudomonas bacteria, the genus Gluconobacter bacteria, the genus Pseudogluconobacter bacteria, the genus Acetobacter bacteria and the like. Specifically, *E. coli* JM109-pUC19SD5 (International Patent Publication No. WO94/20609), *Gluconobacter oxydans* NB6939-pSDH-tufB1, *Gluconobacter oxydans* NB6939-pSDH-trp6, *Gluconobacter oxydans* NB6939-pSDH-PL1, *Gluconobacter oxydans* NB6939-pSDH-tac8 (all from International Patent Publication No. WO95/23220) and the like are exemplified.

The transformant of the present invention can be also obtained by transforming a host cell with an expression vector containing, in addition to the above-mentioned DNA encoding SLDH, a DNA encoding SDH and/or a DNA encoding SNDH in a form permitting expression in the host cell. When the expression vector lacks one of the DNA encoding SDH and the DNA encoding SNDH, the host cell may be co-transformed along with a different expression vector containing said DNA.

The recombinant SLDH of the present invention can be produced by culturing a transformant containing an expression vector containing a DNA encoding the above-mentioned SLDH in a suitable medium and harvesting SLDH from the obtained culture.

The nutrient medium to be used contains, as a carbon source, saccharides such as glucose and fructose, glycerol, preferably L-sorbose and D-sorbitol. It may contain an inorganic or organic nitrogen source (e.g., ammonium sulfate, ammonium chloride, hydrolysate of casein, yeast extract, polypeptone, bactotrypton, beef extract and the like). When desired, other nutrient sources [e.g., inorganic salt (e.g., sodium diphosphate or potassium diphosphate, potassium hydrogenphosphate, magnesium chloride, magnesium sulfate, calcium chloride), vitamins (e.g., vitamin B1), antibiotics (e.g., ampicillin, kanamycin) etc.] may be added to the medium. Preferably, the medium contains D-sorbitol, yeast extract, $CaCO_3$ and glycerol as ingredients. The medium has a sugar (D-sorbitol) concentration of generally 1–50%, preferably 2–40%.

A transformant is cultured at generally pH 5.5–8.5, preferably pH 6–8, at generally 18–40° C., preferably 20–35° C. for 5–150 h.

SLDH can be purified by appropriately combining various separation techniques typically used according to the fraction having an SLDH activity. Since the SLDH of the present invention is $NAD(P)^+$ dependent, it highly likely localizes in a soluble fraction of the transformant. In this case, after the completion of the culture, the culture is filtrated or centrifuged to recover the cell, which is then ruptured by ultrasonication, lysozyme treatment, osmotic pressure shock and the like to give a cell extract for use.

When the recombinant SLDH is produced in the aforementioned form wherein a specific amino acid sequence is added to the terminus, the SLDH can be quickly and easily purified by a treatment including chromatography using a carrier, on which a metal ion chelate capable of adsorbing the specific amino acid sequence is immobilized (immobilized metal affinity chromatography; IMAC). The metal ion chelate adsorber to be used can be prepared by bringing a solution containing a transition metal (e.g., divalent ion such as cobalt, copper, nickel and iron, trivalent ion such as iron, aluminum and the like, preferably divalent ion of cobalt) into contact with a matrix to which a ligand, for example, iminodiacetate group, nitrilotriacetate group, tris (carboxymethyl)ethylenediamine group and the like, has been attached to allow binding with the ligand. The matrix portion of the chelate adsorbent is not particularly limited as long as it is a typical insoluble carrier.

According to the production method of L-sorbose of the present invention, any transformant containing an expression vector containing the above-mentioned DNA encoding SLDH is cultured in a suitable medium, and D-sorbitol is brought into contact with the obtained culture, or, when the SLDH activity is present in an intracellular fraction of the transformant, with a cell extract thereof, to give L-sorbose. The method for bringing D-sorbitol into contact with the culture includes culture of the transformant in a medium containing D-sorbitol.

The present invention also provides a production method of 2KLGA, which utilizes L-sorbose obtained by the above-mentioned method. That is, a host cell capable of converting L-sorbose to 2KLGA, preferably a host cell transformed with an expression vector containing a DNA encoding SDH and a DNA encoding SNDH, is cultured in a suitable medium, and L-sorbose obtained by the above-mentioned method is brought into contact with the obtained culture, or, when the SDH and SLDH activity is present in an intracellular fraction of the host cell, with a cell extract thereof, to give 2KLGA. The method for bringing L-sorbose into contact with the culture includes culture of the host cell in a medium containing L-sorbose.

According to a different production method of 2KLGA of the present invention, a host cell capable of converting L-sorbose to 2KLGA, which is transformed with an expression vector containing a DNA encoding the above-mentioned SLDH, is s cultured in a suitable medium, and D-sorbitol is brought into contact with the obtained culture, or, when the SLDH, SDH and SLDH activity is present in an intracellular fraction of the host cell, with a cell extract thereof, to give 2KLGA. The method for bringing D-sorbitol into contact with the culture includes culture of the host cell in a medium containing D-sorbitol.

The medium and culture conditions to be used for the production method of L-sorbose and the production method of 2KLGA of the present invention may be the same as or partially different from those used for the above-mentioned production method of SLDH.

When D-sorbitol or L-sorbose is brought into contact with a cell extract, the culture after the completion of culture is centrifuged or filtrated to recover the cell, which is suspended in a suitable buffer, such as acetate buffer, and the cell is ruptured by ultrasonication and the like and subjected to a centrifugation treatment to give a supernatant which can be used as a cell extract.

The L-sorbose or 2KLGA thus produced can be purified from a reaction mixture (when the transformant is cultured in a medium containing D-sorbitol or L-sorbose, a culture supernatant) by a purification method generally used (for example, dialysis, gel filtration, column chromatography on a suitable adsorbent, high performance liquid chromatography and the like).

The purified 2KLGA can be converted to L-ascorbic acid or a salt thereof (for example, salt with an alkali metal or alkaline earth metal) by a method conventionally known. Such method is not particularly limited and exemplified by a method including heating 2KLGA by adding a strong acid such as hydrochloric acid.

The present invention is explained in detail in the following by referring to Examples. These examples are merely exemplifications and do not limit the scope of the present invention in any way.

EXAMPLE 1

Cloning of SLDH (1) Preparation of Chromosomal DNA

A single colony of the strain *G. oxydans* G624 (FERM BP-4415; International Patent Publication No. WO95/23220) was cultured in a medium (pH 6.0) containing 2.5% mannitol, 0.3% polypeptone and 0.5% yeast extract at 37° C. for 48 hours. The cells were collected by centrifugation (6,000 rpm, 10 minutes) and suspended in sterilized water (1 ml). The suspension was diluted with STE buffer [1 ml, 20% sucrose—50 mM Tris-HCl (pH 8.0)—1 mM EDTA] and lysozyme (2 mg) was added. The mixture was stood at 37° C. for 30 minutes. Thereto were added a sarcosyl solution [2.5 ml, 1% lauroylsarcosylate 100 mM EDTA (pH 8.5)] and proteinase K (final concentration 100 µg/ml), and the mixture was stood at 50° C. for 2 hours. Thereto were added caesium chloride (5.5 g) and 5 mg/ml ethidium bromide (0.3 ml) and the mixture was ultracentrifuged at 20° C., 50,000 rpm for 16 hours. The part containing a chromosomal DNA was isolated, dissolved in TE buffer [30 ml, 10 mM Tris-HCl (pH 8.0)—1 mM EDTA] and dialyzed twice against 5 L of 1 mM EDTA. The dialyzate was washed 4 times with isobutanol, twice with phenol and 3 times with chloroform, and purified by ethanol precipitation. This was dissolved in TE buffer (10 ml) to give a 160 μg/ml chromosomal DNA solution.

(2) Preparation of Cosmid Library

A single colony of *Escherichia coli* DH1/pcos6EMBL (ATCC is 37571; purchased from ATCC through Sumitomo Pharma International Co. Ltd.) was cultured in a 50 μg/ml kanamycin-containing LB medium [3 ml, 1% polypeptone, 0.5% yeast extract, 1% sodium chloride (pH 7.4)] at 37° C. for 16 hours, and 0.5 ml thereof was inoculated to 50 μg/ml kanamycin-containing LB medium (50 ml) in a 500 ml Erlenmeyer flask. The medium was cultured at 37° C. for 8 hours and the cells were harvested by centrifugation (6,000 rpm, 10 minutes). The cosmid pcos6EMBL was purified with QIAGEN Plasmid Midi Kit (QIAGEN). The pcos6EMBL (25 μg) was digested with 50 U BamHI at 37° C. for 2 hours, and purified by ethanol precipitation. This was subjected to dephosphorylation with 3 U calf intestine-derived alkaline phosphatase (CIAP) at 37° C. for 1 hour and purified by ethanol precipitation. Separately, the chromosomal DNA (100 μg) of the strain *G. oxydans* G624 obtained in the above-mentioned (1) was partially digested with 5 U Sau3AI at 37° C. for 1 minute, and purified by ethanol precipitation. The partial digest (ca. 1.5 μg) and BamHI digest of pcos6EMBL (ca. 3 μg) were ligated with 3 U T4 DNA ligase at 4° C. for 16 hours. A portion (3 μl) thereof was subjected to in vitro packaging using GIGAPACK II Gold Packaging Extract (STRATAGENE). This packaging solution was diluted 50-fold with SM buffer [50 mM Tris-HCl (pH 7.5)—100 mM NaCl—8 mM MgSO$_{4-0.1}$% gelatin] and 25 μl of the indicating bacteria (*Escherichia coli* XL1-Blue MRA) was infected with 25 μl thereof, sown on a 50; g/ml kanamycin-containing LB plate and stood at 37° C. overnight. About 400 colonies were obtained, which means a cosmid library of about 400000 clones was obtained.

(3) Screening of Clone Having SLDH Activity

In a 96 well plate rounded bottom (Nalge) containing a 0.9-fold diluted LB medium containing 5% sorbitol and 50 μg/ml kanamycin by 150 μl per well, 368 cosmid clones were cultured with gentle shaking at 30° C. for 3 days. After centrifugation (2,000 rpm, 10 minutes), 0.5 mg/ml resorcin-ethanol solution (30 μl) and 0.216 mg/ml ferric sulfate (III) ammonium-hydrochloric acid solution (30 μl) were added to the culture supernatant (20 μl), and the mixture was heated at 80° C. for 1 hour. Using a medium alone similarly reacted as a control, 3 clones of 1A4, 1A5, 4A9 which showed deeper brown color than did the control were selected as the clones having a conversion capability to sorbose (fructose). The culture supernatants thereof were analyzed by HPLC [column: Polyspher OA KC (E. Merck), 7.8×300 mm; temperature: room temperature; migration phase: 0.01N H$_2$SO$_4$; flow amount: 0.4 ml/minute; detection: RI] and sorbose was detected for each clone. Thus, these 3 clones were considered to have an SLDH activity. The length of the insert part of these cosmid clones was about 40 kb for all of them.

(4) Subcloning to Charomid Vector (Downsizing of Insert)

The cosmid clone 1A4 (300 ng) having an SLDH activity was partially digested with 20 mU Sau3AI at 37° C. for 1 hour. The charomid 9-28 (1μg, Nippon Gene) was digested with 4 U BamHI at 37° C. for 1 hour. These two solutions were mixed, purified by ethanol precipitation, dissolved in 2-fold diluted TE buffer (5 μl) and ligated with 1 U T4 DNA ligase at 4° C. for 16 hours. One(1) μl thereof was subjected to in vitro packaging using GIGAPACK II XL Packaging Extract (STRATAGENE). The packaging solution (75 μl) and SM buffer (75 μl) were mixed and used for infecting 150 μl of indicating bacteria (*Escherichia coli* DH-1), which was sown on a 50 μg/ml ampicillin-containing LB plate and incubated at 37° C. for 1 day. Of the colonies appeared, 95 colonies were cultured with gentle shaking at 30° C. for 3 days in a 96 well plate rounded bottom (Nalge) containing a 0.9-fold diluted LB medium containing 5% sorbitol and 50 μg/ml kanamycin by 150 μl per well. After centrifugation (2,000 rpm, 10 minutes), 0.5 mg/ml resorcin-ethanol solution (30 μl/ and 0.216 mg/ml ferric sulfate (III) ammonium-hydrochloric acid solution (30 μl) were added to the culture supernatant (20 μl/, and the mixture was heated at 80° C. for 1 hour. Using a medium alone similarly reacted as a control, 6 clones of G1, C2, A4, B7, H10, B12 which showed deeper brown color than did the control were selected as the clones having a conversion capability to sorbose. The length of the insert part of these charomid clones was about 15 kb for all of them.

(5) Subcloning of SLDH Gene to Plasmid Vector

From the restriction enzyme map of the clones obtained so far, it was found that SLDH gene did not have a SacI site or a XbaI site. Thus, 1 μg of charomid B7 was digested with 10 U of SacI and 10 U of XbaI to give about 6 kb (B7SX3) and about 9 kb (B7SX2) SacI-XbaI fragments. These two fragments were respectively ligated with *Escherichia coli*-Pseudomonas shuttle vector pUCP19 [1.8 kb PstI fragment derived from pRO1614 was inserted into NarI site of pUC19 and purified from *Escherichia coli* DH5 αF' (ATCC 87110)] and transformed with Pseudomonas (this strain was later named Pseudomonas sp. F-1, hereinafter to be referred to by this designation) by the electroporation method to give Ps./pUCP19-B7SX3 and Ps./pUCP19-B7SX2. The preparation of competent cell and conditions of transformation followed those of *Escherichia coli*. These two clones were cultured in a medium containing sorbitol. As a result, sorbose conversion capability was found in Ps./pUCP19-B7SX2. Therefore, Ps./pUCP19-B7SX2 was cultured in a medium (pH 7.4) containing 5% sorbitol, 1% bactotrypton, 0.5% yeast extract, 1% sodium chloride and 50 μg/ml ampicillin at 30° C. for 4 days to give 2.4 mg/ml of sorbose (conversion efficiency: 5%). This sorbose was separated by HPLC and the coincidence of retention time with the standard product was confirmed. HPLC was performed under the same conditions as in the above-mentioned (3). Using GC/MS [column:DB-5 (J & W Scientific), 0.32 mm×30 m (film 0.25 μm); temperature: injection=230° C., column= 100° C. (5 minutes)→heating at 10° C./minute for 10 minute→200° C. (5 minutes)→heating at 30° C./minute for 1 minute→230° C. (4 minutes), detect=230° C.; flow amount: pressure control 20 kPa(He)], the coincidence of mass pattern with the standard product was confirmed.

(6) Determination of Base Sequence of SLDH Gene

Figure 2:
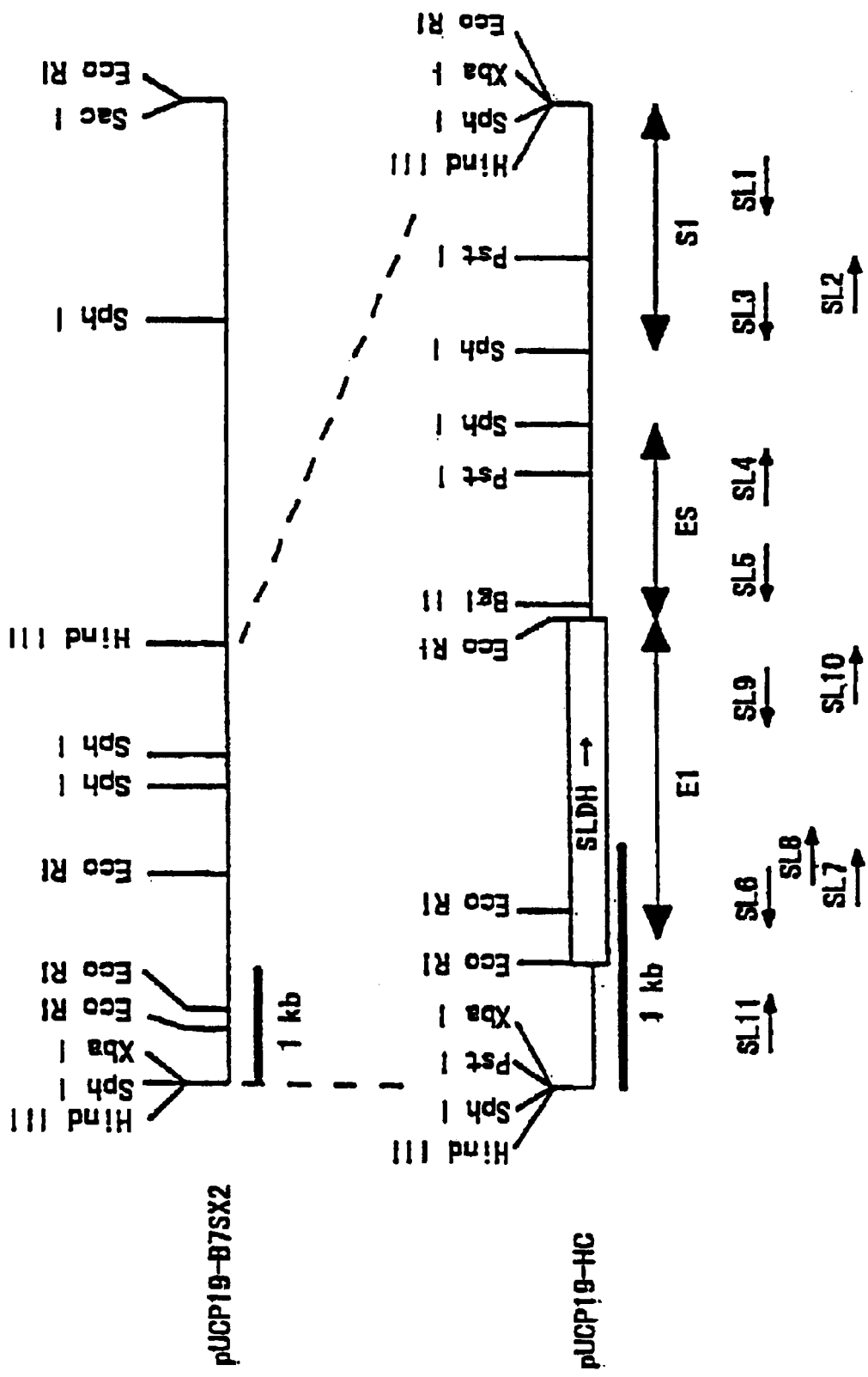
FIG. 2 shows a restriction enzyme map of DNA insert portion of plasmids pUCP19-B7SX2 and pUCP19-HC, and a sequencing strategy of the DNA insert portion of pUCP19-HC.

The restriction enzyme map of the insert part of plasmid pUCP19-B7SX2 of transformant of Pseudomonas, Ps./pUCP19-B7SX2, that expresses an SLDH activity was assumed as shown in FIG. 2. By digestion of 1 μg of pUCP19-B7SX2 with 10 U of Hind III at 37° C. for 1 hour, about 4 kb Hind III—Hind III fragment was obtained. This Hind III—Hind III fragment was ligated with vector pUCP19 and plasmid pUCP19-HC was constructed. Pseudomonas was transformed with this plasmid to give Ps./pUCP19-HC. This transformant was cultured in a medium containing sorbitol. As a result, expression of SLDH activity was acknowledged. Thus, this Hind III—Hind III fragment was found to contain full length SLDH gene. The base sequence of this about 4 kb Hind III—Hind III fragment was determined. First, the insert part of pUCP19-HC was divided into about 1.1 kb SphI—SphI fragment (S1), about 0.8 kb EcoRI-SphI fragment (ES) and about 1.3 kb EcoRI—EcoRI (E1) fragment (FIG. 2), and each was subcloned to pUC18 to give pUC18-S1, pUC18-ES and pUC18-E1.

Using plasmids pUCP19-HC, pUC18-S1, pUC18-ES and pUC18E1 as templates and using universal primer and reverse primer (New England Labs.), which were M 13 sequencing primers, first sequencing was performed. The sample was fluorescent labeled with BigDye Terminator Cycle Sequencing kit (Applied Biosystems) and analyzed with ABI PRISM 310 Genetic Analyzer (Applied Biosystems). The following 11 kinds of primers were synthesized and using pUCP19-HC as a template sequencing was performed, whereby the base sequence of about 4 kb Hind IIIHind III fragment was determined (Sequence Listing SEQ ID NO:1.

SLDH Gene Sequencing Primer

SL1 GCTGCTGAGTGATCCG (Sequence Listing SEQ ID NO:3)

SL2 GACTGCTACTTCGATCC (Sequence Listing SEQ ID NO:4)

SL3 CCTACACCTAGCCTGC (Sequence Listing SEQ ID NO:5)

SL4 CAGTGCCGTCATGAGG (Sequence Listing SEQ ID NO:6)

SL5 TCCTGATCTCGGTGCG (Sequence Listing SEQ ID NO:7)

SL6 GATGCTTCAGCACGGC (Sequence Listing SEQ ID NO:8)

SL7 GACGATCACGGAAGGC (Sequence Listing SEQ ID NO:9)

SL8 GGTTACGTGGTCGAGG (Sequence Listing SEQ ID NO:10)

SL9 CTATACGTGACAGGTCC (Sequence Listing SEQ ID NO:11)

SL10 GCGCGATCTGGATACG (Sequence Listing SEQ ID NO:12)

SL11 CGAGGATCTCGAACGG (Sequence Listing SEQ ID NO:13)

From the analysis of the base sequence, 1455 bp ORF was found (base number 537–1991). Therefore, SLDH was assumed to consist of 485 amino acids and has a molecular weight of about 54 kDa. As a result of the homology search, it showed 42% homology with mannitol dehydrogenase of *Pseudomonas fluorescence*.

EXAMPLE 2

Production of Recombinant SLDH (1) Construction of Plasmid Expressing SLDH Having Histidine-tag (Hereinafter to be Referred to as His-tagged SLDH)

For purification of the recombinant protein, a tag system utilizing 6×histidine was an extremely easy method. That is, a protein having 6 histidine tag is expressed, and utilizing interaction of a metal (e.g., cobalt, nickel) and histidine residue, the protein is separated by IMAC. For insertion of 6×His into the C terminus side of SLDH, the following two pairs of primers were respectively used and using pUCP19-HC (5 ng) as a template, PCR was performed with pfu DNA polymerase (2.5 U) (94° C., 30 seconds→55° C. 2 minutes→72° C., 2 minutes, 25 cycles). The primer (each 20 pmol) was heated to 99° C. for 4 minutes and rapidly cooled before use.

PCR 1

Primer 1 (sense) [sequence that coincides with sequence near NheI site (underlined) in SLDH coding sequence]

CGGATT<u>GCTAGC</u>GATGGC (Sequence Listing SEQ ID NO:14)

Primer 2 (antisense) [containing sequence that coincides with 3' terminus of SLDH coding sequence, 6×His (H), stop is codon (*) and BamHI site (underlined part)]

```
ATCGAGGATCC TCA ATGATGATGATGATGATG GGCCGGGATGGCGGC   (Sequence Listing SEQ ID NO:15)
          *  H  H  H  H  H  H
```

PCR 2

Primer 3 (sense) [including BamHI site (underlined) and sequence that coincides with sequence immediately after stop codon of SLDH gene]

ATCGA<u>GGATCC</u>ATTCGGCTTTTAGGGTAGC (Sequence Listing SEQ ID NO:16)

Primer 4 (antisense) [including sequence that coincides with sequence near BglII site in 3' non-coding region of SLDH gene and SacI site (underlined)]

TAGCT<u>GAGCTC</u>ATGGGACAGATCTGAGC (Sequence Listing SEQ ID NO:17)

Figure 3:
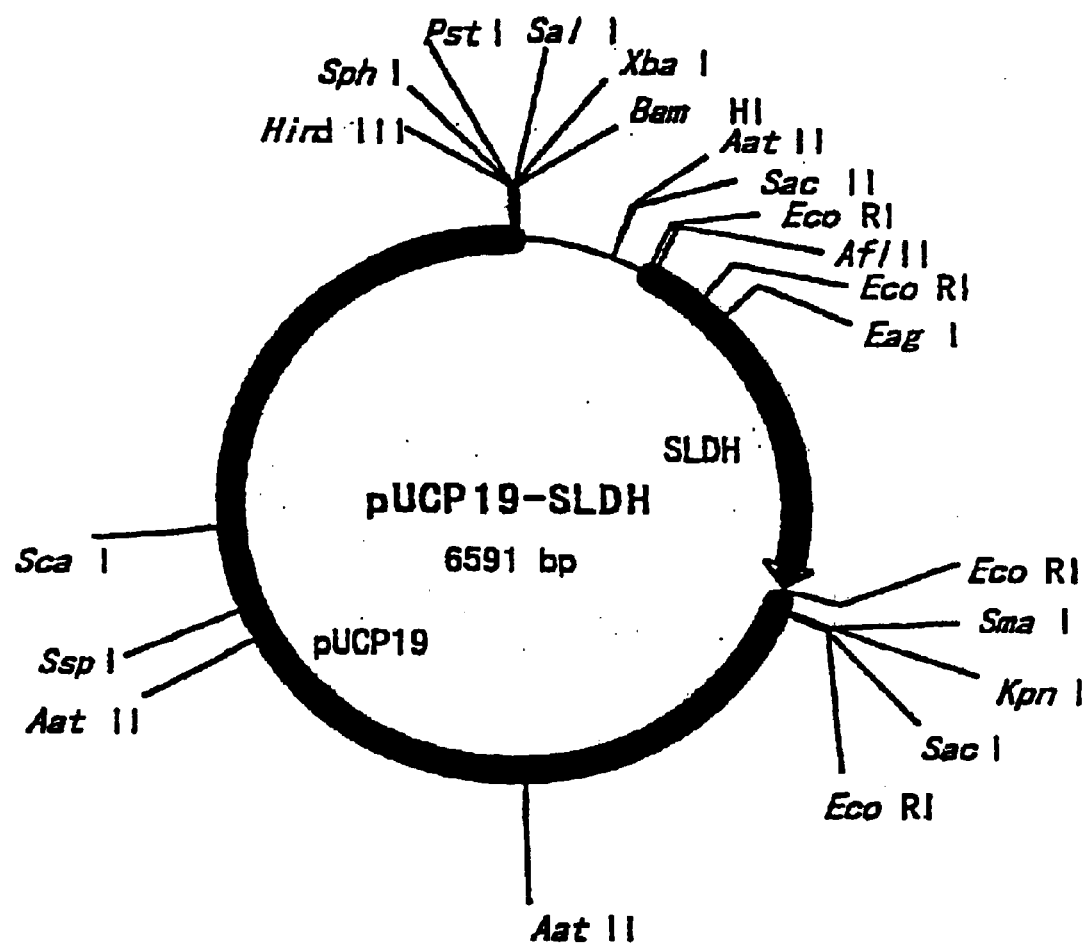
FIG. 3 shows a gene map of plasmid pUCP19-SLDH.

The about 360 bp fragment specifically amplified in PCR 1 was digested with NheI and BamHI, and the about 100 bp fragment specifically amplified in PCR 2 was digested with BamHI and SacI. Separately, the about 2 kb fragment obtained by digesting pUCP19-HC with BglII and PstI was inserted into BamHI-PstI fragment of pUCP19 to give plasmid pUCP19-SLDH (FIG. 3) wherein the downstream of BglII site of the insert was removed. This was digested with NheI and SacI, and the obtained about 6.2 kb fragment was ligated with the above-mentioned two PCR amplification fragments with T4 DNA ligase to construct pUCP19-SLDH-His. Pseudomonas was transformed with this plasmid to give Ps./pUCP19-SLDH-His.

(2) Purification of His-tagged SLDH

One loopful of cryopreservation stock of transformant Ps./pUCP19-SLDH-His was inoculated to LB medium (2 ml) containing 50 μg/ml ampicillin in a 15 ml centrifuge tube (Corning) and cultured at 30° C. for 16 hours. The 1.5 ml thereof was inoculated to LB medium (50 ml) containing 5% sorbitol and 50 μg/ml ampicillin in a 500 ml Erlenmeyer flask and cultured at 25° C. for 3 days. The cells were harvested by centrifugation (6,000 rpm, 4° C. for 5 minutes), and suspended in 10 ml of 100 mM NaCl-containing 20 mM Tris-HCl (pH 8.0). The suspension was treated with an ultrasonication homogenizer (Tomy UD-201) for 5 minutes (50% interval), centrifuged (15,000 rpm, 4° C. for 10 minutes) and a supernatant was recovered to give a cell-free extract. TARON resin (2 ml, CLONTECH) was placed in a 15 ml centrifuge tube (Corning), and washed twice with 10 ml of 100 mM NaCl-containing 20 mM Tris-HCl (pH 8.0) for equilibration. The above-mentioned cell-free extract (5 ml) was added and the mixture was shaken at room temperature for 20 minutes to adsorb His-tagged SLDH, followed by washing 3 times with 100 mM NaCl-containing 20 mM Tris-HCl (10 ml, pH 8.0) over 10 minutes. 100 mM NaCl-containing 20 mM Tris-HCl buffers (2 ml, pH 8.0) respectively containing 10 mM, 30 mM, 50 mM and 100 mM imidazole were added successively, and shaken at room temperature for 2 minutes to elute His-tagged SLDH. As a is result, SLDH activity eluted in a 30 mM–50 mM imidazole fraction. This fraction was applied to SDS-PAGE analyze to detect nearly single band.

(3) Analysis of N terminus Amino Acid Sequence

The His-tagged SLDH purified in the above-mentioned (2) was electrophoresed using a multigel (Daiichi Pure Chemicals) having a gel concentration of 12.5% with 40 mA current over 1 hour, and using Horiz-Blot (Atto), transferred onto a PVDF membrane (Immobilon PSQ; Millipore). The membrane was stained with coomasie brilliant blue G-250, and a band seemingly an about 55 kDa SLDH was cut out with a pair of scissors. This PVDF membrane was subjected to amino acid sequence analysis using protein sequencer G100A (Hewlett-Packard) and PTH analyzer 1090 (Hewlett-Packard). As a result, a sequence (MITRETLKSL; Sequence Listing SEQ ID NO:18) consistent with N terminus amino acid sequence expected from ORF of SLDH gene was obtained.

(4) Confirmation of SLDH Activity

In the same manner as in the above-mentioned (2) except that the cell-free extract to be applied was by 10 ml, the resin after His-tagged SLDH adsorption was washed 6 times, and His-tagged SLDH was eluted with 50 mM imidazole and 100 mM NaCl-containing 20 mM Tris-HCl (5 ml, pH 8.0), His-tagged SLDH was purified. The obtained His-tagged SLDH was reacted with sorbitol and the resulting product was analyzed. The composition of the reaction solution (2 ml) was 10 mM (1.82 mg/ml) sorbitol, 0.1 M glycine/NaOH buffer (pH 10.1), 5 mM NADP$^+$ and His-tagged SLDH 0.2 ml (41.4 μg protein) and the reaction was carried out at 25° C. for 24 hours. As a result, 1.12 mg/ml sorbose was generated (sorbitol remaining in 0.70 mg/ml; conversion efficiency: 62%). Thus, His-tagged SLDH purified by cobalt type IMAC was confirmed to be sorbitol dehydrogenase that oxidizes sorbitol and generates sorbose.

EXAMPLE 3

Characterization of SLDH (1) Coenzyme Dependency and Active pH Range

To a solution containing 0.1 ml of 50 mM NAD$^+$ (or NADP$^+$), 0.2 ml of 500 mM buffer, 10 μl of His-tagged SLDH solution (2.1 μg protein) prepared in Example 2(4) and distilled water (0.29 ml) was added to 500 mM sorbitol (0.4 ml) to start the reaction (25° C.), and increase in NADH (or NADPH) was measured by a spectrophotometer (UV-2200; Shimadzu) based on absorbance at 340 nm as an index. For the reaction solutions having pH 10.1 and pH 9.0, glycine/NaOH buffer was used, and for reaction solutions having pH 8.0 and pH 7.0, potassium phosphate buffer was used. The enzyme activity (1 unit) was defined to be an amount to generate 1 μmol of NADH (or NADPH) per minute. The molecular extinction coefficient of NAD(P)H was 6.3 mM$^{-1}$ cm$^{-1}$. The protein amount was measured with bovine serum albumin (BSA) as a standard by the Lowry method. As a result, SLDH could utilize both NAD$^+$ and NADP$^+$ as coenzymes, and NADP$^+$ showed higher specificity. The activity of this enzyme was higher in the alkaline pH (Table 1).

TABLE 1

| Coenzyme | pH | Activity (U/mg protein) |
|---|---|---|
| NADP$^+$ | 10.1 | 130.2 |
|  | 9.0 | 30.0 |
|  | 8.0 | 22.9 |
|  | 7.0 | 4.2 |
| NAD$^+$ | 10.1 | 8.1 |
|  | 9.0 | 3.4 |
|  | 8.0 | 1.2 |
|  | 7.0 | 0.1 |

(2) Substrate Specificity

In the same manner as in the above-mentioned (1) except that the reaction solution contained various substrates to replace sorbitol, the buffer was glycine/NaOH buffer (pH 10.1), and coenzyme was NADP+, the SLDH activity was measured. As a result, this enzyme could utilize, besides sorbitol, mannitol and arabitol as a substrate, but showed no action on xylitol, ribitol, inositol or glycerol (Table 2).

TABLE 2

| Substrate | Activity (U/mg protein) |
|---|---|
| sorbitol | 130.2 |
| mannitol | 85.7 |
| arabitol | 88.1 |
| xylitol | 0 |
| ribitol | 0 |
| inositol | 0 |
| glycerol | 0 |

(3) Michaelis Constant

Using sorbitol as a substrate, SLDH activity was measured according to the method of the above-mentioned (2). As a result, the Km value for sorbitol was 132 mM (25° C.).

EXAMPLE 4

Preparation of Pseudomonas Transformant Having SNDH/SDH Expression Vector and Study of 2KLGA Productivity by this Transformant Of the pBBR plasmids that are broad host range plasmids [Gene, 166, 175 (1995)] supplied by Dr. Kovach at Louisiana State University, Medical Center, SNDH/SDH gene was introduced into the genus Pseudomonas strain using pBBR1MCS-2 (kanamycin resistant) and pBBR1MCS-3 (tetracycline resistant) as vectors, and fermentative production of 2KLGA from L-sorbose by the obtained transformant was studied.

(1) Construction of SNDH/SDH Expressing Broad Host Range Plasmid

Figure 4:
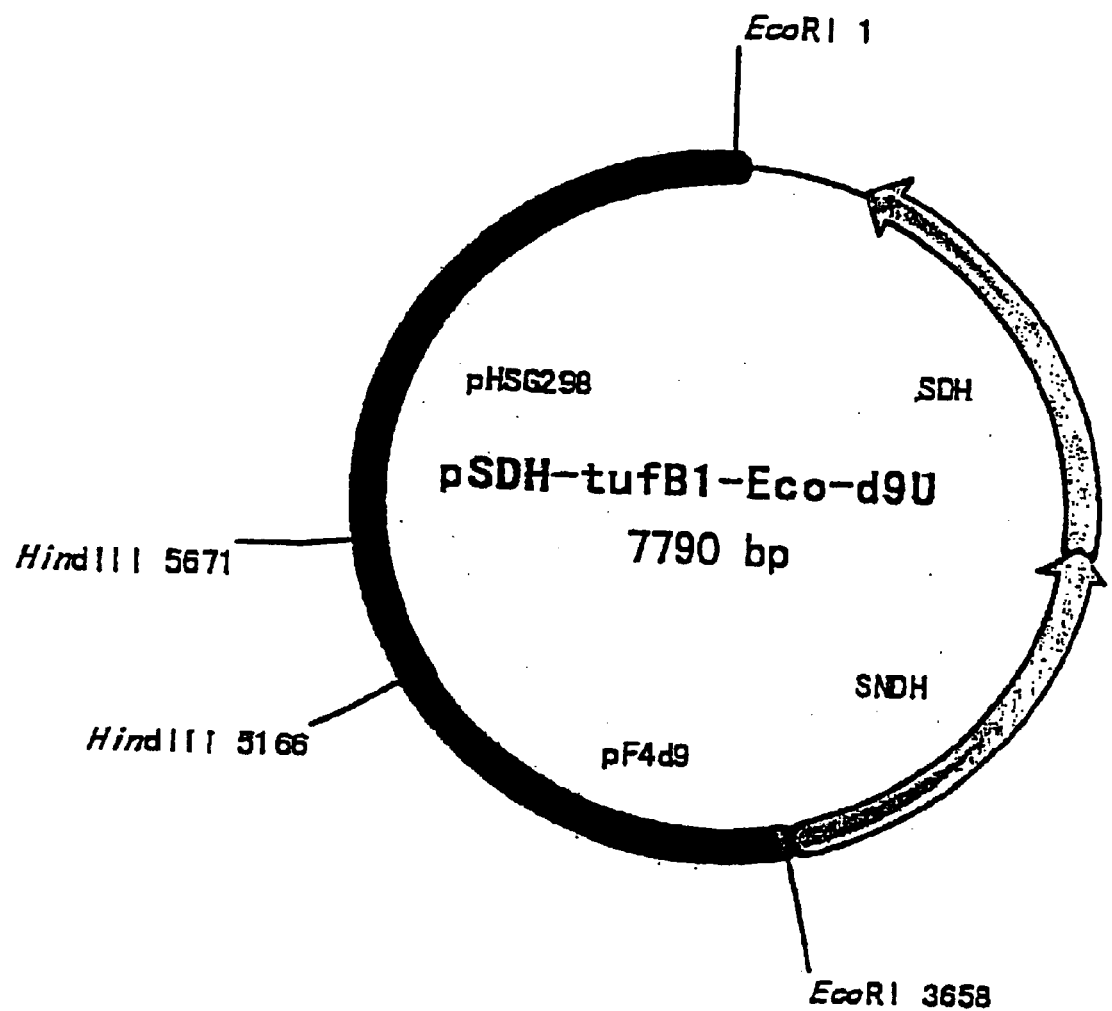
FIG. 4 shows a gene map of expression vector pSDH-tufB1-Eco-d9U.
Figure 5:
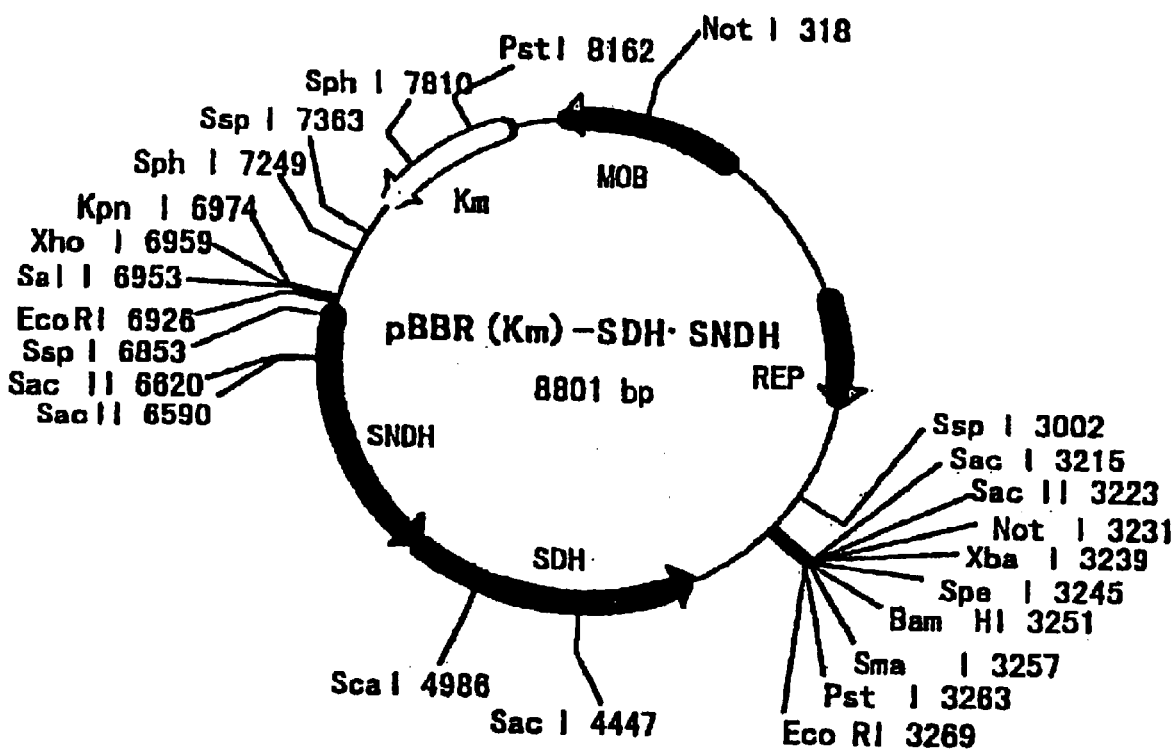
FIG. 5 shows a gene map of expression vector pBBR (Km)-SDH.SNDH.

Plasmid pSDH-tufB1-Eco-d9U (FIG. 4) (5 μg) containing SNDH/SDH gene and using tufB as a promoter was digested with EcoRI (50 U, Behringer-Mannheim) at 37° C. for 1 hour, and electrophoresed on 0.8% agarose gel, which was followed by separation of a 3.7 kb EcoRI/EcoRI fragment containing SNDH/SDH gene. This fragment was inserted into the EcoRI site of pBBR1MCS-2. The plasmid inserted in the same direction as the β-galactosidase gene was taken as pBBR (Km)-SDH.SNDH (FIG. 5).

Figure 6:
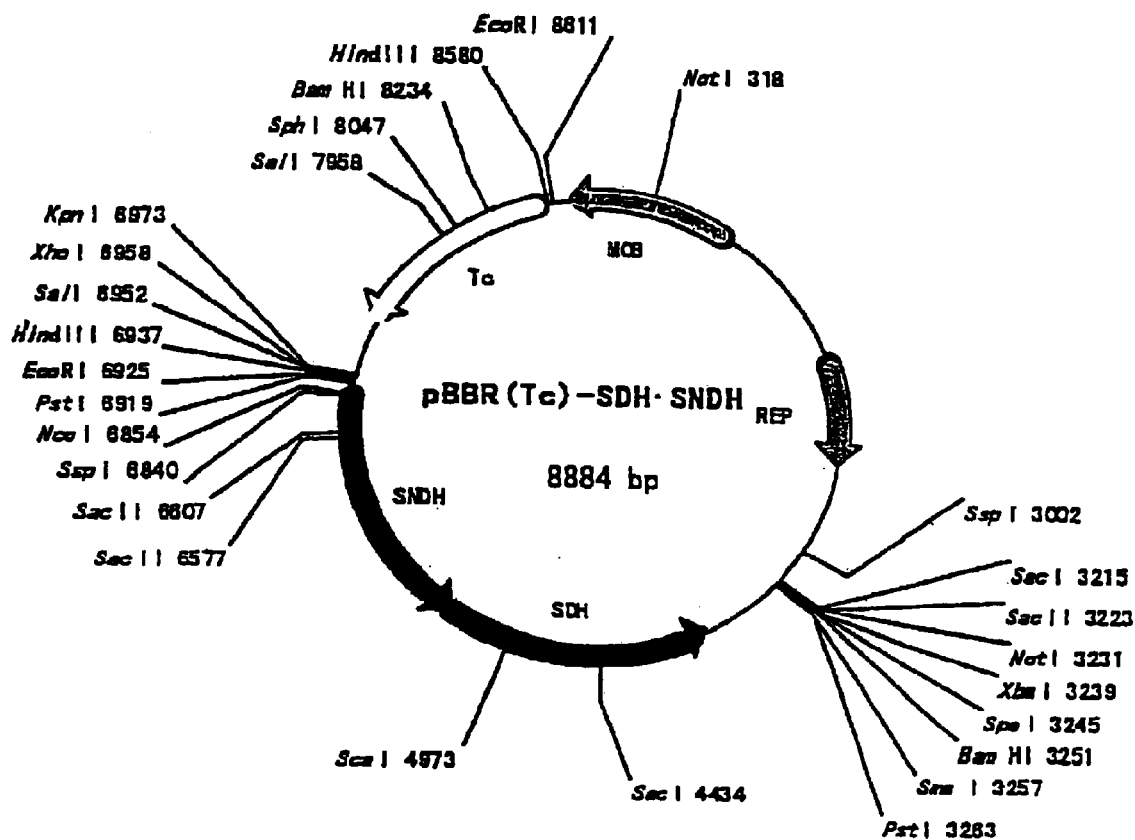
FIG. 6 shows a gene map of expression vector pBBR (Tc)-SDH.SNDH.

Plasmid pSDH-tufB1 (10 μg, construction method is described in European Patent Publication EP 0758679 A1) containing an SNDH/SDH gene and using tufB as a promoter was digested with EcoRI (50 U, Behringer-Mannheim) at 37° C. for 1 hour and the termini were blunted by a treatment using Klenow fragment (Nippon Gene) at room temperature for 30 minutes. Using a T4 DNA ligase (TOYOBO), PstI linker (GCTGCAGC, TOYOBO) was ligated with the termini and digested with PstI (50 U, Behringer Mannheim) at 37° C. for 1 hour. This digest was electrophoresed with 0.8% agarose gel and a 3.7 kb PstI/PstI fragment containing an SNDH/SDH gene was separated. This fragment was inserted in the PstI site of pBBR1MCS-3. The plasmid inserted in the same direction as the β-galactosidase gene was taken as pBBR(Tc)SDH.SNDH (FIG. 6).

(2) Preparation of Competent Cell of Pseudomonas

The glycerol cryopreservation stock of Pseudomonas sp.F-1 was inoculated to L medium (3 ml, pH 7.4) containing 1% bactotrypton (Difco), 0.5% yeast extract (Difco) and 1% sodium chloride in a 16.5×165 mm test tube and cultured at 30° C. overnight. The entire amount of the culture solution was inoculated to L medium (50 ml) in a 500 ml Erlenmeyer flask, and cultured at 25° C. for 6 hours. The culture solution was centrifuged to harvest the cells and the cells were washed twice with cold 10% aqueous glycerol solution (30 ml). The washed cells were suspended in a small amount of cold 10% aqueous glycerol solution, dispensed by 60 μl and instantaneously frozen with liquid nitrogen.

(3) Transformation of Pseudomonas

The competent cells of Pseudomonas cryopreserved in liquid nitrogen sp.F-1 were thawed in ice water, and solutions of an SNDH/SDH expressing broad host range plasmid constructed in the above-mentioned (1), pBBR(Km)-SDH.SNDH and pBBR(Tc)-SDH.SNDH, were added by 1 μl (ca. 1 μg) each, and stood at 4° C. for 30 minutes. This was transformed using a Gene Pulser gene transfer device (Rio-Rad) in a cuvette having a distance of 0.1 cm between electrodes under the conditions of 200Ω, 1.8 μV, 25 μF, and suspended in L medium containing 0.4% glucose, which was followed by shaking at 30° C. for 1 hour. They were sown on an L agar plate containing 50 μg/ml kanamycin and an L agar plate containing 20 μg/ml tetracycline, cultured at 30° C. for 2 days to give transformant Ps./pBBR(Km)-SDH.SNDH and Ps./pBBR(Tc)-SDH.SNDH.

(4) Fermentative Production of 2KLGA from Sorbose by the Transformant

A single colony of transformants Ps./pBBR(Km)-SDH.SNDH and Ps./pBBR (Tc)-SDH 90H obtained in the above-mentioned (3) was each inoculated to 5 ml of L medium in a 16.5×165 mm test tube and cultured at 30° C. for 2 days. The culture solution (0.5 ml) was inoculated to a medium (10 ml, pH 7.4) for 2KLGA production containing 5% sorbose, 0.1% glucose, 0.9% bactotrypton (Difco), 0.45% yeast extract (Difco), 0.9% sodium chloride and 2% calcium carbonate in a 100 ml Erlenmeyer flask, and cultured at 30° C. for 5 days. The culture solution was separated by centrifugation and sorbose, sorbosone, 2KLGA and L-idonic acid in the culture supernatant were quantitatively determined. The sorbose, sorbosone, 2KLGA and L-idonic acid were each quantitatively determined by HPLC under the following conditions.

[sorbose]
  column: Polyspher OA KC (7.8 mm inner diameter×300 mm; Cica-MERCK)
  migration phase: 0.01N $H_2SO_4$
  column temperature: room temperature
  flow rate: 0.4 ml/minute
  detection: differential refractometer
[sorbosone (post-column labeling method)]
  column: Polyspher OA KC (7.8 mm inner diameter×300 mm; Cica-MERCK)
  migration phase (labeling agent): 0.04M benzamidine hydrochloride
  0.25M potassium sulfite
  2 mM boric acid/0.1N potassium hydroxide
  flow rate: 0.3 ml/minute
  detection: fluorescent detector (excitation wavelength: 315 nm, detection wavelength: 405 nm)
[2KLGA and L-idonic acid]
  column: Capcell pak NH2 (4.6 mm inner diameter×250 mm; Shiseido)
  migration phase: 30% acetonitrile, 20 mM calcium phosphate (pH 3.0)
  flow rate: 1.2 ml/minute
  detection: UV-210 nm As a result, the conversion efficiency from sorbose to 2KLGA by Ps./pBBR(Km)-SDH.SNDH was about 18%, and about 37% combined with the conversion efficiency to L-idonic acid. The conversion efficiency from sorbose to 2KLGA by Ps./pBBR(Tc)-SDH SNDH was about 26%, and about 47% combined with the conversion efficiency to L-idonic acid (Table 3).

TABLE 3

| | culture results by transformant (mg/ml) | | | |
|---|---|---|---|---|
| transformant | sorbose | sorbosone | 2KLGA | L-idonic acid |
| Ps./pBBR(Km)-SDH SNDH | 12.5 (25.0) | 0.3 (0.6) | 8.9 (17.8) | 9.6 (19.6) |
| Ps./pBBR(Tc)-SDH SNDH | 15.6 (31.2) | 0.15 (0.3) | 13 (26.0) | 10.3 (20.6) |

The figures in parentheses are conversion efficiency (% of product concentration to initial sorbose concentration).

For comparison, production of 2KLGA and L-idonic acid by a non-transformant Pseudomonas sp. F-1 was also investigated. The glycerol cryopreserved cells of Pseudomonas sp. F-1 were inoculated to 5 ml of L medium in a 16.5×165 mm test tube and cultured at 30° C. for 1 day. The culture solution (1 ml) was inoculated to a medium (10 ml, pH 7.4) containing 5% sorbose, 0.9% bactotrypton (Difco), 0.45% yeast extract (Difco) and 0.9% sodium chloride in a 100 ml Erlenmeyer flask, and cultured at 30° C. for 3 days. The culture solution was centrifuged and sorbose, sorbosone, 2KLGA and L-idonic acid in the culture supernatant were similarly determined quantitatively. As a result, sorbose was consumed (5.7 mg/ml) but sorbosone, 2KLGA and L-idonic acid were not detected.

From the above, by the introduction of SNDH/SDH gene into 2KLGA and L-idonic acid non-producing Pseudomonas sp. F-1, a transformant that highly produces 2KLGA and L-idonic acid from sorbose could be obtained.

EXAMPLE 5

Preparation of Pseudomonas Transformant Containing SNDH/SDH Expression Vector and Consideration of 2KLGA Productivity of the Transformant—(2)

In the same manner as in Example 4 and using a different strain [strain Pseudomonas IFO3309; supplied by the Institute for Fermentation, Osaka (17-85, Juso-honmachi 2-chome, Yodogawa-ku, Osaka)] belonging to the genus Pseudomonas as a host, a transformant was prepared, into which the SNDH/SDH gene was introduced, and the 2KLGA and L-idonic acid productivity of this transformant was investigated.

(1) Introduction of SNDH/SDH Gene into Strain Pseudomonas IFO3309

Glycerol cryopreserved cells of the strain Pseudomonas IFO3309 were treated in the same manner as in Example 4(2) to prepare cryopreserved cells of competent cells. The competent cells cryopreserved in liquid nitrogen were thawed in ice water, and a solution 1 μl (ca. 1 μg) of Ps./pBBR(Km)-SDH.SNDH, which was an SNDH/SDH expressing broad host range plasmid, was added and the mixture was stood at 4° C. for 30 minutes. This was transformed using a Gene Pulser gene transfer device (Bio-Rad) under the same conditions as in Example 4(3) to give transformant Ps. IFO3309/pBBR(Km)-SDH.SNDH.

(2) Fermentative Production of 2KLGA by the Transformant

One loopful of the Ps.IFO3309/pBBR(Km)-SDH.SNDH obtained in the above (1) was inoculated to a medium (5 ml, pH 7.0) containing 2% sorbitol and 0.5% yeast extract (Difco) in a 16.5×165 mm test tube, and cultured at 28° C. for 1 day. The culture solution (1 ml) was inoculated to a medium (10 ml, pH 7.0) containing 5% sorbitol, 0.5% yeast extract (Difco), 0.2% polypeptone (Wako Pure Chemical Industries), 0.1% $K_2HPO_4$, 0.5% $MgSO_4.7H_2O$ and 2% $CaCO_3$ in a 100 ml Erlenmeyer flask and cultured at 28° C. for 7 days. The culture solution was centrifuged and in the same manner as in Example 4(4), sorbitol, sorbose, sorbosone, 2KLGA and L-idonic acid in the culture supernatant were quantitatively determined. For comparison, non-transformant the strain Pseudomonas IFO3309 was cultured under the same conditions and sorbitol, sorbose, sorbosone, 2KLGA and L-idonic acid in the culture supernatant were quantitatively determined.

As a result, by the non-transformant, sorbitol was consumed (0.4 mg/ml), sorbose was produced (3.9 mg/ml) but sorbosone, 2KLGA and L-idonic acid were not detected. On the other hand, 2KLGA (1.2 mg/ml) and L-idonic acid (0.5 mg/ml) were produced by the transformant Ps. IFO3309/pBBR(Km)-SDH.SNDH (Table 4). In other words, it was confirmed that, by the introduction of SNDH/SDH gene into this host, the ability to produce 2KLGA and L-idonic acid from sorbitol was imparted even under the conditions where Pseudomonas IFO3309 cannot produce 2KLGA or L-idonic acid.

TABLE 4

| transformant | culture results by transformant (mg/ml) | | | |
| --- | --- | --- | --- | --- |
| | sorbose | sorbosone | 2KLGA | L-idonic acid |
| Ps.3309/pBBR(Km)-SDH SNDH | 0.41 | 1.8 | 1.2 | 0.5 |

EXAMPLE 6

Production of 2KLGA by Pseudomonas Transformant into which SLDH Expression Vector and SNDH/SDH Expression Vector were Introduced (1) Preparation of Pseudomonas Transformant having SLDH Expression Vector and SNDH/SDH Expression Vector As mentioned above, an expression vector pBBR(Km)-SDH.SNDH (FIG. 5) was constructed by incorporating an SNDH/SDH gene derived from G. oxydans T-100 (FERM BP-4188; European Patent Publication EP 0758679 A1) into pBBR1MCS-2. pBBR(Km)-SDH.SNDH was introduced into recombinant Pseudomonas Ps./pUCP19-B7SX2 obtained in Example 1(5) by the electroporation method to give Ps./pUCP19-B7SX2+pBBR(Km)-SDH.SNDH.

(2) Production of 2KLGA by Pseudomonas Transformant

Ps./pUCP19-B7SX2+pBBR(Km)-SDH.SNDH was cultured in a medium (pH 7.4) containing 5% sorbitol, 1% bactotrypton (Difco), 0.5% yeast extract (Difco), 1% sodium chloride, 50 μg/ml ampicillin, 50 μg/ml kanamycin and 2% light calcium carbonate at 30° C. for 4 days to give 1.1 mg/ml of 2KLGA and 1.7 mg/ml of idonic acid. The 2KLGA was separated by HPLC and coincidence with a standard product in the retention time was confirmed. Using GC/MS, coincidence with a standard product in the mass pattern was confirmed. HPLC and GC/MS were performed under the same conditions as in Example 1(3) and (5).

EXAMPLE 7

Preparation of Various Pseudomonas Transformants
(1) Ps./pUCP19-SLDH+pBBR(Km)-SDH.SNDH Pseudomonas sp.F-1 was transformed with pUCP19-SLDH constructed in Example 2(1) to give Ps./pUCP19-SLDH. pBBR(Km)-SDH SNDH was further introduced into this recombinant Pseudomonas to give Ps./pUCP19-SLDH+pBBR(Km)-SDH.SNDH.

(2) Ps./pUCP19-SLDH-tufB+pBBR(Km)-SDH.SNDH

To introduce SspI site into the upstream of initiation codon of SLDH gene, PCR was performed using pUCP19-SLDH (5 μg) as a template in the presence of the following primers (20 pmol each) using pfu DNA polymerase (2.5 U) (94° C., 30 seconds→55° C., 2 minutes→72° C., 2 minutes, 25 cycles). sense primer [including SspI site (underlined) and sequence identical with 5' terminus of SLDH coding sequence]

TAGGAATATTTCTCATGATTACGCGCGAAACCC
(Sequence Listing SEQ ID NO:19)

antisense primer [sequence identical with sequence downstream of EagI site in SLDH coding sequence]

GATGCTTCAGCACGGC (Sequence Listing SEQ ID NO:20)

The about 360 bp fragment specifically amplified by PCR was digested with SspI and EagI. pUCP19-SLDH was digested with PstI and EagI to give about 5.7 kb fragment. These two fragments and PstI-SspI fragment (Sequence Listing SEQ ID NO:21) containing tufB promoter were ligated with T4 DNA ligase to construct pUCP19-SLDH-tufB. Pseudomonas was transformed with this plasmid to give Ps./pUCP19-SLDH-tufB. Furthermore, pBBR(Km)-SDH.SNDH capable of expressing SNDH/SDH activity was introduced to give Ps./pUCP19-SLDH-tufB+pBBR(Km)-SDH.SNDH.

Figure 7:
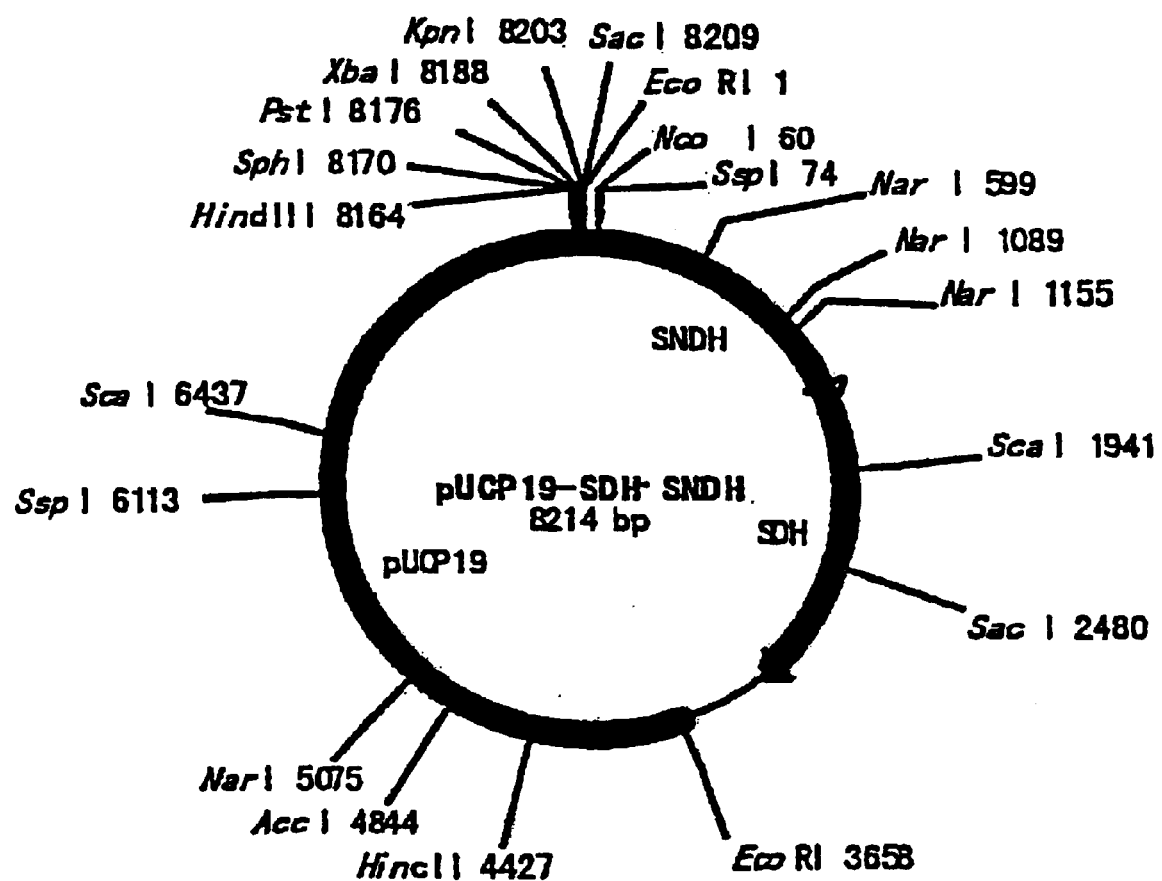
FIG. 7 shows a gene map of expression vector pUCP19-SDH.SNDH.

(3) Ps./pUCP19-3DH pUCP19-SLDH-tufB (5 μg) was digested with 40 U KpnI and 40 U PstI at 37° C. for 1 hour to give a 1.6 kb fragment. pUCP19-SDH.SNDH (expression vector obtained by incorporating SNDH/SDH gene derived from G. oxydans T-100 into pUCP19; FIG. 7) (1 μg) was digested with 10 U KpnI and 10 U PstI at 37° C. for 1 hour to give a 8.2 kb fragment. These two fragments were ligated with T4 DNA ligase to construct pUCP19–3DH. Pseudomonas was transformed with this plasmid to give Ps./pUCP19-3DH.

EXAMPLE 8

Consideration of Productivity of 2KLGA

Since production of 2KLGA by recombinant Pseudomonas was confirmed, the productivity of 2KLGA was studied in media having various compositions by 4 transformants obtained in Examples 6 and 7.

[culture 1]

One loopful of cryopreservation stock of Ps./pUCP19-B7SX2+pBBR(Km)-SDH.SNDH was inoculated to a medium (2 ml, pH 7.4) containing 1% bactotrypton (Difco), 0.5% yeast extract (Difco), 1% NaCl, 50 µg/ml ampicillin and 50 µg/ml kanamycin in a 15 ml tube (Falcon) and pre-cultured at 30° C. for 24 hours. The pre-culture solution (0.5 ml) was inoculated to a main culture medium (10 ml, pH 7.0) containing 5% sorbitol, 5% yeast extract (Difco), 0.15% MgSO$_4$.7H$_2$O, 50 µg/ml ampicillin, 50 µg/ml kanamycin and 4% calcium carbonate in a 100 ml Erlenmeyer flask and cultured at 30° C. for 3 days.

[culture 2]

The cells were cultured in the same manner as in [culture 1] except that 5% yeast extract in the main culture medium was changed to 5% casamino acid.

[culture 3]

The cells were cultured in the same manner as in [culture 1] except that 1% glycerol was further added to the main culture medium.

[culture 4]

The cells were cultured in the same manner as in [culture 1] except that Ps./pUCP19-SLDH+pBBR(Km)-SDH.SNDH was used as the producing bacteria and 5% glycerol was further added to the main culture medium.

[culture 5]

The cells were cultured in the same manner as in [culture 1] except that Ps./pUCP19-SLDH-tufB+pBBR(Km)-SDH.SNDH was used as the producing bacteria and 5% glycerol was further added to the main culture medium.

[culture 6]

The cells were cultured in the same manner as in [culture 1] except that Ps./pUCP19-3DH was used as the producing bacteria, kanamycin was removed from the pre-culture medium and the main culture medium and 5% glycerol was further added to the main culture medium.

The sorbitol, sorbose, sorbosone and 2KLGA in each culture were quantitatively determined. The results are shown in Table 5. The propensity toward increased conversion efficiency to 2KLGA was observed by the addition of glycerol to the medium.

[culture 7]

The cells were cultured for 7 days in the same manner as in [culture 1] except that the yeast extract concentration of the main culture medium was set to 2% and 5% glycerol was further added to the main culture medium. The sorbitol, sorbose, sorbosone and 2KLGA at day 1, 3, 5 and 7 of culture were quantitatively determined. The results are shown in Table 5.

TABLE 5

| culture | | sorbitol | sorbose | sorbosone | 2KLGA | idonic acid |
|---|---|---|---|---|---|---|
| 1 | | 44.1 | 6.3 | 0.1 | 3.7 | 1.6 |
| 2 | | 44.8 | 3.1 | 0 | 4.8 | 2.2 |
| 3 | | 26.7 | 5.1 | 0 | 10.9 | 8.4 |
| 4 | | 26.6 | 0 | 0 | 9.0 | ND |
| 5 | | 26.6 | 0 | 0 | 10.7 | ND |
| 6 | | 30.7 | 5.2 | 0 | 7.5 | ND |
| | days | | | | | |
| 7 | 1 | 41.1 | 0 | 0 | 4.2 | ND |
| | 3 | 25.6 | 0 | 0 | 10.6 | ND |
| | 5 | 14.2 | 0 | 0 | 16.3 | ND |
| | 7 | 7.6 | 0 | 0 | 18.4 | 15.5 |

(unit: mg/ml)
ND: Not determined

EXAMPLE 9

Fermentative Production of Sorbose or 2KLGA by *Pseudomonas putida* Transformant into which SLDH Expression Vector and/or SNDH/SDH Expression Vector were Introduced In the following test, the preparation and transformation of competent cells of the strain *Pseudomonas putida* IFO3738 followed the above-mentioned Pseudomonas sp.F-1. Because the strain *Pseudomonas putida* IFO3738 is ampicillin resistant, when ampicillin resistance is used as a selection marker, cells were sown on an L agar plate containing 500 µg/ml ampicillin (10-fold amount of normal level) after electroporation, and cultured at 30° C. for 1 day to pick up large colonies for the selection of transformant.

(1) Fermentative Production of Sorbose from Sorbitol by Transformant into which SLDH Expression Vector was Introduced SLDH gene (pUCP19-SLDH) was introduced into the strain *Pseudomonas putida* IFO3738. A single colony of the obtained transformant *Pseudomonas putida* IFO3738/pUCP19-SLDH was inoculated to a medium (10 ml, pH 7.4) for sorbose production, which contained 5% sorbitol, 0.9% bactotrypton (Difco), 0.45% yeast extract (Difco), 0.9% sodium chloride and 500 µg/ml ampicillin in a 100 ml Erlenmeyer flask and cultured at 30° C. for 3 days. The culture solution was is centrifuged and sorbitol and sorbose in the culture supernatant were quantitatively determined. As a result, 34.6 mg/ml of sorbitol remained and 7.6 mg/ml of sorbose was generated.

(2) Fermentative Production of 2KLGA from Sorbose by Transformant into which SNDH/SDH Expression Vector was Introduced SNDH/SDH gene (pBBR(Km)-SDH.SNDH) was introduced into *Pseudomonas putida* IFO3738. A single colony of the obtained transformant *Pseudomonas putida* IFO3738/pBBR(Km)-SDH.SNDH was inoculated to a medium (10 ml, pH 7.4) for 2KLGA production, which contained 5% sorbose, 0.9% bactotrypton (Difco), 0.45% yeast extract (Difco), 0.9% sodium chloride, 2% calcium carbonate and 50 µg/ml kanamycin in a 100 ml Erlenmeyer flask and cultured at 30° C. for 7 days. The culture solution was centrifuged and sorbose, 2KLGA and idonic acid in the culture supernatant were quantitatively determined. As a result, 34.3 mg/ml of sorbose remained and 13.9 mg/ml of 2KLGA and 3.5 mg/ml of idonic acid were generated.

(3) Fermentative Production of 2KLGA from Sorbitol by Transformant into which SLDH Expression Vector and SNDH/SDH Expression Vector were Introduced SLDH and SNDH/SDH genes (pUCP19-SLDH and pBBR(Km)-SDH.SNDH) were introduced into the strain *Pseudomonas putida* IFO3738. A single colony of the obtained transformant *Pseudomonas putida* IFO3738/pUCP19-SLDH+pBBR(Km) -SDH.SNDH was inoculated to a medium (10 ml, pH 7.4) for 2KLGA production, which contained 5% sorbitol, 0.9% bactotrypton (Difco), 0.45% yeast extract (Difco), 0.9% sodium chloride, 2% calcium carbonate, 500 µg/ml ampicillin and 50 µg/ml kanamycin in a 100 ml Erlenmeyer flask and cultured at 30° C. for 7 days. The culture solution was centrifuged and sorbitol, sorbose, 2KLGA and idonic acid in the culture supernatant were quantitatively determined. As a result, 35.6 mg/ml of sorbitol remained and 13.2 mg/ml of 2KLGA and 6.2 mg/ml of idonic acid were generated. Sorbose was not detected.

Free Text of Sequence Listing

SEQ ID NO:3: oligonucleotide designed to act as primer for sequencing insert DNA of pUCP19-HC.

SEQ ID NO:4: Oligonucleotide designed to act as primer for sequencing insert DNA of pUCP19-HC.

SEQ ID NO:5: Oligonucleotide designed to act as primer for sequencing insert DNA of pUCP19-HC.

SEQ ID NO:6: Oligonucleotide designed to act as primer for sequencing insert DNA of pUCP19-HC.

SEQ ID NO:7: Oligonucleotide designed to act as primer for sequencing insert DNA of pUCP19-HC.

SEQ ID NO:8: oligonucleotide designed to act as primer for sequencing insert DNA of pUCP19-HC.

SEQ ID NO:9: Oligonucleotide designed to act as primer for sequencing insert DNA of pUCP19-HC.

SEQ ID NO:10: Oligonucleotide designed to act as primer for sequencing insert DNA of pUCP19-HC.

SEQ ID NO:11: Oligonucleotide designed to act as primer for sequencing insert DNA of pUCP19-HC.

SEQ ID NO:12: Oligonucleotide designed to act as primer for sequencing insert DNA of pUCP19-HC.

SEQ ID NO:13: Oligonucleotide designed to act as primer for sequencing insert DNA of pUCP19-HC.

SEQ ID NO:14: Oligonucleotide designed to act as sense primer for amplifying DNA sequence encoding His-tagged SLDH and promoter.

SEQ ID NO:15: Oligonucleotide designed to act as antisense primer for amplifying DNA sequence encoding His-tagged SLDH and promoter.

SEQ ID NO:16: Oligonucleotide designed to act as sense primer for amplifying DNA sequence of 3' non-coding region of SLDH gene.

SEQ ID NO:17: Oligonucleotide designed to act as antisense primer for amplifying DNA sequence of 3' non-coding region of SLDH gene.

SEQ ID NO:18: N-terminal amino acid sequence of SLDH.

SEQ ID NO:19: oligonucleotide designed to act as PCR primer (sense) for introducing SspI restriction site into 5' upstream region of SLDH coding sequence.

SEQ ID NO:20: Oligonucleotide designed to act as PCR primer (antisense) for introducing SspI restriction site into 5' upstream region of SLDH coding sequence.

This application is based on patent application Nos. 72810/1999 and 224679/1999 filed in Japan, the contents of which are hereby incorporated by reference.

All of the references cited herein, including patents and patent applications are hereby incorporated in their entireties by reference.

What is claimed is:

1. An isolated sorbitol dehydrogenase having the following physicochemical properties:
   (a) action: catalyzes the reaction converting D-sorbitol to L-sorbose;
   (b) molecular weight: about 54 kDa;
   (c) coenzyme: NAD (P)$^+$ dependent; and
   (d) substrate specificity: specifically oxidizes sorbitol, mannitol and arabitol, but does not act on xylitol, ribitol, inositol or glycerol,
   wherein said sorbitol dehydrogenase is derived from the stain *Gluconobacter oxydans* G624.

2. An isolated polypeptide comprising SEQ ID NO: 2 or a fragment of SEQ ID NO:2 which has sorbitol dehydrogenase activity.

3. The polypeptide of claim 2, which comprises SEQ ID NO: 2.

4. The polypeptide of claim 2, which comprises a fragment of SEQ ID NO: 2, which has sorbitol dehydrogenase activity.

5. The polypeptide of claim 2, which consists of SEQ ID NO: 2.

* * * * *

SEQUENCE LISTING

```
<160> NUMBER OF SEQ ID NOS: 20

<210> SEQ ID NO 1
<211> LENGTH: 4115
<212> TYPE: DNA
<213> ORGANISM: Gluconobacter oxydans
<220> FEATURE:
<221> NAME/KEY: CDS
<222> LOCATION: (537)..(1994)
<223> OTHER INFORMATION:

<400> SEQUENCE: 1
aagcttgcat gcctgcaggt cgactctaga ggatccggtt ttggcagcgc tccctagatt      60
gatgcggcgt ctgttgaccg acatgatgct ggtggcacgt gccattgcga cggggcgtgc     120
gaccgggaac acaggcctgc tgcctttgta caagggctg agtcatgcgc tgcgtgggct      180
ggcacatagt tgcgaagagc agttgcgcgc aaagcagaac cagcatgaac agcagtccga     240
agacgaggaa atcctcggcc tcctaccgcg attggaagag cagacccgtc ctgagatgcg     300 tttgtgatg tccctgttcc gcgaggatct cgaacgggct gttggggtgc tcatgcgttc     360
tgatgcgagt gccgcaaaag gtctctgaac aggacgtccc gcggagggca gtcagaggtc     420
gaaatggctc ctgttgaaac cgtcattcgg tttttacgtt gtttcggggc tatgatggca     480
catgcccggc cttgtcggtc cccgtcagcg accggcccga aaccacggag aattcc atg    539
                                                                      Met
                                                                       1 att acg cgc gaa acc ctt aag tct ctt cct gcc aat gtc cag gct ccc      587
Ile Thr Arg Glu Thr Leu Lys Ser Leu Pro Ala Asn Val Gln Ala Pro
         5                  10                  15 ccc tat gac atc gac ggg atc aag cct ggg atc gtg cat ttc ggt gta      635
Pro Tyr Asp Ile Asp Gly Ile Lys Pro Gly Ile Val His Phe Gly Val
     20                  25                  30 ggt aac ttt ttt cga gcc cat gag gcg ttc tac gtc gag cag att ctt      683
Gly Asn Phe Phe Arg Ala His Glu Ala Phe Tyr Val Glu Gln Ile Leu
```

```
              35                  40                  45
gaa cac gct ccg gac tgg gcg att gtt ggt gtt ggc ctg acg ggc agt     731
Glu His Ala Pro Asp Trp Ala Ile Val Gly Val Gly Leu Thr Gly Ser
 50              55                  60                  65 gac cgt tca aag aaa aaa gcc gag gaa ttc aag gcc cag gac tgc ctg     779
Asp Arg Ser Lys Lys Lys Ala Glu Glu Phe Lys Ala Gln Asp Cys Leu
                 70                  75                  80 tat tcc ctg acc gag acg gct ccg tcc ggc aag agc acg gtg cgc gtc     827
Tyr Ser Leu Thr Glu Thr Ala Pro Ser Gly Lys Ser Thr Val Arg Val
             85                  90                  95 atg ggc gcg ctg cgt gac tat ctg ctt gcc ccg gcc gat ccg gaa gcc     875
Met Gly Ala Leu Arg Asp Tyr Leu Leu Ala Pro Ala Asp Pro Glu Ala
        100                 105                 110 gtg ctg aag cat ctt gtt gat ccg gcc atc cgc atc gtt tcc atg acg     923
Val Leu Lys His Leu Val Asp Pro Ala Ile Arg Ile Val Ser Met Thr
    115                 120                 125 atc acg gaa ggc ggc tac aac atc aac gag acg acc ggt gcg ttc gat     971
Ile Thr Glu Gly Gly Tyr Asn Ile Asn Glu Thr Thr Gly Ala Phe Asp
130                 135                 140                 145 ctg gag aat gcg gca gta aag gcc gac ctc aag aac ccg gaa aag ccg    1019
Leu Glu Asn Ala Ala Val Lys Ala Asp Leu Lys Asn Pro Glu Lys Pro
                150                 155                 160 tct acc gtt ttc ggt tac gtg gtc gag gcc ctg cgt cgt cgt tgg gat    1067
Ser Thr Val Phe Gly Tyr Val Val Glu Ala Leu Arg Arg Arg Trp Asp
            165                 170                 175 gcc ggt ggt aag gca ttt acg gtc atg tcc tgt gat aac ctg cgt cat    1115
Ala Gly Gly Lys Ala Phe Thr Val Met Ser Cys Asp Asn Leu Arg His
        180                 185                 190 aac ggc aat gtc gcc cgc aag gcc ttc ctc ggc tat gcg aag gcg cgc    1163
Asn Gly Asn Val Ala Arg Lys Ala Phe Leu Gly Tyr Ala Lys Ala Arg
    195                 200                 205 gat ccg gag ttg gcg aag tgg att gag gaa aac gcg acc ttc ccg aac    1211
Asp Pro Glu Leu Ala Lys Trp Ile Glu Glu Asn Ala Thr Phe Pro Asn
210                 215                 220                 225 gga atg gtt gat cgc atc acc ccg acc gtt tcg gcg gaa atc gcc aag    1259
Gly Met Val Asp Arg Ile Thr Pro Thr Val Ser Ala Glu Ile Ala Lys
                230                 235                 240 aag ctc aac gcg gcc agt ggg ctg gat gac gac ctg ccg ctg gtg gcc    1307
Lys Leu Asn Ala Ala Ser Gly Leu Asp Asp Asp Leu Pro Leu Val Ala
            245                 250                 255 gag gat ttc cat cag tgg gtg ctg gaa gac cag ttt gcg gat ggc cgt    1355
Glu Asp Phe His Gln Trp Val Leu Glu Asp Gln Phe Ala Asp Gly Arg
        260                 265                 270 ccg ccg ctt gaa aaa gcc ggc gtg cag atg gtc ggg gac gtg acg gac    1403
Pro Pro Leu Glu Lys Ala Gly Val Gln Met Val Gly Asp Val Thr Asp
    275                 280                 285 tgg gag tac gtc aag atc cga atg ctc aat gca ggg cat gtc atg ctc    1451
Trp Glu Tyr Val Lys Ile Arg Met Leu Asn Ala Gly His Val Met Leu
290                 295                 300                 305 tgc ttc cca ggc att ctg gtc ggc tat gag aat gtg gat gac gcc att    1499
Cys Phe Pro Gly Ile Leu Val Gly Tyr Glu Asn Val Asp Asp Ala Ile
                310                 315                 320 gaa gac agc gaa ctc ctt ggc aat ctg aag aac tat ctc aac aag gat    1547
Glu Asp Ser Glu Leu Leu Gly Asn Leu Lys Asn Tyr Leu Asn Lys Asp
            325                 330                 335 gtc atc ccg acc ctg aag gcg cct tca ggc atg acg ctc gaa ggc tat    1595
Val Ile Pro Thr Leu Lys Ala Pro Ser Gly Met Thr Leu Glu Gly Tyr
        340                 345                 350 cgg gac agc gtc atc agc cgt ttc tcc aac aag gcg atg tcg gac cag    1643
```

```
Arg Asp Ser Val Ile Ser Arg Phe Ser Asn Lys Ala Met Ser Asp Gln
    355                 360                 365 acg ctc cgg att gct agc gat ggc tgt tcc aag gtt cag gtg ttc tgg    1691
Thr Leu Arg Ile Ala Ser Asp Gly Cys Ser Lys Val Gln Val Phe Trp
370                 375                 380                 385 acg gaa acc gtg cgt cgg gcg atc gaa gac aag cgg gac ctg tca cgt    1739
Thr Glu Thr Val Arg Arg Ala Ile Glu Asp Lys Arg Asp Leu Ser Arg
                390                 395                 400 ata gcg ttc gga att gca tcc tat ctc gaa atg ctg cgt ggt cgc gac    1787
Ile Ala Phe Gly Ile Ala Ser Tyr Leu Glu Met Leu Arg Gly Arg Asp
            405                 410                 415 gag aag ggc ggg acg tat gaa tcg tcc gag ccg act tat ggc gac gcc    1835
Glu Lys Gly Gly Thr Tyr Glu Ser Ser Glu Pro Thr Tyr Gly Asp Ala
        420                 425                 430 gaa tgg aag ttg gcc aag gcg gac gac ttc gaa agc tct ctg aag ctc    1883
Glu Trp Lys Leu Ala Lys Ala Asp Asp Phe Glu Ser Ser Leu Lys Leu
    435                 440                 445 ccg gcg ttc gat ggg tgg cgc gat ctg gat acg tcc gaa ctg gat caa    1931
Pro Ala Phe Asp Gly Trp Arg Asp Leu Asp Thr Ser Glu Leu Asp Gln
450                 455                 460                 465 aag gtc atc gtg ctg cgg aag atc atc cgc gaa aag ggc gta aaa gcc    1979
Lys Val Ile Val Leu Arg Lys Ile Ile Arg Glu Lys Gly Val Lys Ala
                470                 475                 480 gcc atc ccg gcc tga attcggcttt tagggtagcg actgaaacag aaaaccgcgc    2034
Ala Ile Pro Ala
            485 tctggaagga gcgcggtttt ttttatgctc agatctgtcc catcaggaca aggatcacga    2094
cgaccacgat caggacaagt ccgctggagg gggagcccca tttcgaactg tacggccatg    2154
acggcagcgc accgagatca ggattacaag aaggatcagt cccatggcac atctctcttg    2214
ccggttgaga ctggtctgtg ttccgggtgt ctaaaaagtt tccgtagggg cgcgaaagat    2274
caaagctgtc ggtcgcgctt aatccggtcc caagccgcat tgatgcgggc cacccggtcc    2334
tgtgcgcgtt tgcgctctgt ctctgacata ggtttctggg ccagcacgtc cggatgatgt    2394
tcgcggatca gggtgcgcca gcgcacgcgg atttctgtgt cagttgcgct gcgggtgatg    2454
ccgagaatac gataggcatc cggctcgttt ccgctggcgg cgcgattgtt gccgctttcg    2514
gcccgtcccc atgctcctgg cggcaggcca atgccccgt gaacgcgctg cagaaaatcg    2574
atttccttcg ggtgaagctc gcggctgggg ccggcatcgg cacgggcgat acggaacagt    2634
gccgtcatga ggtctcaag cggcgccgta ttatcggcat aggccttgcc catttcgcgg    2694
gcatacatct cgaaatcgtc cgtccggtcg cgggcgcgat cgaacagcat gccgacttcc    2754
ttggtgttat cgggggggaa ctggaagcag gtcttgaaag cgttgatttc gtgtcggttc    2814
accggcccgt cgatcttcgc cagcttcgcg cacagggcaa caaggccgat ggcgtaaagc    2874
tgatctcgtt tgcccagggc cgcagcaatc ttggcagcgc cgaaaaaggc cgcgctgttg    2934
ggatcgggac ggccattcgc gggaaagcgc tcactccagc cgcccgttga gggcttgagt    2994
agcgaaccgt tatcggcggc atgccccagc gctgcgccca tcagtgctcc gaaaggacca    3054
ccaaccgcga agcccgcgac accaccgaac atcttgcccc agatagccat gtcatcaacc    3114
tagcacgccc gctcacagcg gcaaatgaca gatcgcaggc taggtgtagg tgctgatgcg    3174
ccaaccgccc gggcttgcgg tgtggtagaa gctaggagtt acgaacttat cgctgtctca    3234
tgcttttgag gcgcaggttc ttctgttcgt ttcatgacgg atattttat gcccaccttg    3294
atccagactg ctacttcgat ccctttccgc tctgatgacg aactgatgga tcttttgatc    3354
```

```
aagcgtctgc caatgtggct gcagaaagtg ctgaactggt tgcgggaagc ggatcataaa    3414
tgggttcgga ttccggcggg cgtgctgttc atgctgggcg gcgttctgtc catcctgcct    3474
gttctgggtc tgtggatgct gccggtcggc gtgatgttgc ttgcgcagga tattccgttc    3534
ttccgtcgcc ttcagggccg cctcttgcgc tggatcgaac gtcaacatcc ggattggctg    3594
ggccttccgg cgaaaagcgg cagaagctaa ccgttcgtct ggacgtgttt ctgaagatgt    3654
gtcagtgctg caacccgcag ggctgaagcc agtgggcgct ctggtggtcg cgcggcatcg    3714
agagaagcca ccagagacgc aaagctctgc tggcggactg cggccatcgc gtccagtata    3774
gcccagaact cgggttccag tgccacggac gtccggtgtc ctgacagaga caggctgcgt    3834
ttgacgagat cactcattcc ggttgtttct caaggcgctt caaagcccat tgtgcggttt    3894
cggaaacatc agggtccgga tcactcagca gctcccgcgc agaagatata agcgacggat    3954
cggccgagtt gccgatcgcg atcaggacag ttacgtacga accggttgcg tccaatccgt    4014
ttgaccggag agccagaaaa aaacgtccgg aatgtcgcat tatccagccg caccagttcg    4074
tcgagttttg gtgcaatcag ctccgggcgg gcctgaagct t                        4115
```

<210> SEQ ID NO 2
<211> LENGTH: 485
<212> TYPE: PRT
<213> ORGANISM: Gluconobacter oxydans

<400> SEQUENCE: 2

```
Met Ile Thr Arg Glu Thr Leu Lys Ser Leu Pro Ala Asn Val Gln Ala
 1               5                  10                  15

Pro Pro Tyr Asp Ile Asp Gly Ile Lys Pro Gly Ile Val His Phe Gly
                20                  25                  30

Val Gly Asn Phe Phe Arg Ala His Glu Ala Phe Tyr Val Glu Gln Ile
            35                  40                  45

Leu Glu His Ala Pro Asp Trp Ala Ile Val Gly Val Gly Leu Thr Gly
        50                  55                  60

Ser Asp Arg Ser Lys Lys Ala Glu Phe Lys Ala Gln Asp Cys
65                  70                  75                  80

Leu Tyr Ser Leu Thr Glu Thr Ala Pro Ser Gly Lys Ser Thr Val Arg
                85                  90                  95

Val Met Gly Ala Leu Arg Asp Tyr Leu Leu Ala Pro Ala Asp Pro Glu
            100                 105                 110

Ala Val Leu Lys His Leu Val Asp Pro Ala Ile Arg Ile Val Ser Met
        115                 120                 125

Thr Ile Thr Glu Gly Gly Tyr Asn Ile Asn Glu Thr Thr Gly Ala Phe
    130                 135                 140

Asp Leu Glu Asn Ala Ala Val Lys Ala Asp Leu Lys Asn Pro Glu Lys
145                 150                 155                 160

Pro Ser Thr Val Phe Gly Tyr Val Val Glu Ala Leu Arg Arg Arg Trp
                165                 170                 175

Asp Ala Gly Gly Lys Ala Phe Thr Val Met Ser Cys Asp Asn Leu Arg
            180                 185                 190

His Asn Gly Asn Val Ala Arg Lys Ala Phe Leu Gly Tyr Ala Lys Ala
        195                 200                 205

Arg Asp Pro Glu Leu Ala Lys Trp Ile Glu Glu Asn Ala Thr Phe Pro
    210                 215                 220

Asn Gly Met Val Asp Arg Ile Thr Pro Thr Val Ser Ala Glu Ile Ala
225                 230                 235                 240
```

-continued

```
Lys Lys Leu Asn Ala Ala Ser Gly Leu Asp Asp Leu Pro Leu Val
            245                 250                 255

Ala Glu Asp Phe His Gln Trp Val Leu Glu Asp Gln Phe Ala Asp Gly
                260                 265                 270

Arg Pro Pro Leu Glu Lys Ala Gly Val Gln Met Val Gly Asp Val Thr
            275                 280                 285

Asp Trp Glu Tyr Val Lys Ile Arg Met Leu Asn Ala Gly His Val Met
            290                 295                 300

Leu Cys Phe Pro Gly Ile Leu Val Gly Tyr Glu Asn Val Asp Asp Ala
305                 310                 315                 320

Ile Glu Asp Ser Glu Leu Leu Gly Asn Leu Lys Asn Tyr Leu Asn Lys
                325                 330                 335

Asp Val Ile Pro Thr Leu Lys Ala Pro Ser Gly Met Thr Leu Glu Gly
            340                 345                 350

Tyr Arg Asp Ser Val Ile Ser Arg Phe Ser Asn Lys Ala Met Ser Asp
            355                 360                 365

Gln Thr Leu Arg Ile Ala Ser Asp Gly Cys Ser Lys Val Gln Val Phe
            370                 375                 380

Trp Thr Glu Thr Val Arg Arg Ala Ile Glu Asp Lys Arg Asp Leu Ser
385                 390                 395                 400

Arg Ile Ala Phe Gly Ile Ala Ser Tyr Leu Glu Met Leu Arg Gly Arg
                405                 410                 415

Asp Glu Lys Gly Gly Thr Tyr Glu Ser Ser Glu Pro Thr Tyr Gly Asp
            420                 425                 430

Ala Glu Trp Lys Leu Ala Lys Ala Asp Asp Phe Glu Ser Ser Leu Lys
            435                 440                 445

Leu Pro Ala Phe Asp Gly Trp Arg Asp Leu Asp Thr Ser Glu Leu Asp
            450                 455                 460

Gln Lys Val Ile Val Leu Arg Lys Ile Arg Glu Lys Gly Val Lys
465                 470                 475                 480

Ala Ala Ile Pro Ala
            485
```

<210> SEQ ID NO 3
<211> LENGTH: 16
<212> TYPE: DNA
<213> ORGANISM: Artificial Sequence
<220> FEATURE:
<223> OTHER INFORMATION: synthetic DNA

<400> SEQUENCE: 3
gctgctgagt gatccg                                                  16

<210> SEQ ID NO 4
<211> LENGTH: 17
<212> TYPE: DNA
<213> ORGANISM: Artificial Sequence
<220> FEATURE:
<223> OTHER INFORMATION: synthetic DNA

<400> SEQUENCE: 4
gactgctact tcgatcc                                                 17

<210> SEQ ID NO 5
<211> LENGTH: 16
<212> TYPE: DNA
<213> ORGANISM: Artificial Sequence
<220> FEATURE:
<223> OTHER INFORMATION: synthetic DNA

```
<400> SEQUENCE: 5
cctacaccta gcctgc                                                    16

<210> SEQ ID NO 6
<211> LENGTH: 16
<212> TYPE: DNA
<213> ORGANISM: Artificial Sequence
<220> FEATURE:
<223> OTHER INFORMATION: synthetic DNA

<400> SEQUENCE: 6
cagtgccgtc atgagg                                                    16

<210> SEQ ID NO 7
<211> LENGTH: 16
<212> TYPE: DNA
<213> ORGANISM: Artificial Sequence
<220> FEATURE:
<223> OTHER INFORMATION: synthetic DNA

<400> SEQUENCE: 7
tcctgatctc ggtgcg                                                    16

<210> SEQ ID NO 8
<211> LENGTH: 16
<212> TYPE: DNA
<213> ORGANISM: Artificial Sequence
<220> FEATURE:
<223> OTHER INFORMATION: synthetic DNA

<400> SEQUENCE: 8
gatgcttcag cacggc                                                    16

<210> SEQ ID NO 9
<211> LENGTH: 16
<212> TYPE: DNA
<213> ORGANISM: Artificial Sequence
<220> FEATURE:
<223> OTHER INFORMATION: synthetic DNA

<400> SEQUENCE: 9
gacgatcacg gaaggc                                                    16

<210> SEQ ID NO 10
<211> LENGTH: 16
<212> TYPE: DNA
<213> ORGANISM: Artificial Sequence
<220> FEATURE:
<223> OTHER INFORMATION: synthetic DNA

<400> SEQUENCE: 10
ggttacgtgg tcgacg                                                    16

<210> SEQ ID NO 11
<211> LENGTH: 17
<212> TYPE: DNA
<213> ORGANISM: Artificial Sequence
<220> FEATURE:
<223> OTHER INFORMATION: synthetic DNA

<400> SEQUENCE: 11
ctatacctga caggtcc                                                   17

<210> SEQ ID NO 12
```

```
<211> LENGTH: 16
<212> TYPE: DNA
<213> ORGANISM: Artificial Sequence
<220> FEATURE:
<223> OTHER INFORMATION: synthetic DNA

<400> SEQUENCE: 12
gcgcgatctg gatacg                                                      16

<210> SEQ ID NO 13
<211> LENGTH: 16
<212> TYPE: DNA
<213> ORGANISM: Artificial Sequence
<220> FEATURE:
<223> OTHER INFORMATION: synthetic DNA

<400> SEQUENCE: 13
cgaggatctc gaacgg                                                      16

<210> SEQ ID NO 14
<211> LENGTH: 18
<212> TYPE: DNA
<213> ORGANISM: Artificial Sequence
<220> FEATURE:
<223> OTHER INFORMATION: synthetic DNA

<400> SEQUENCE: 14
cggattgcta gcgatggc                                                    18

<210> SEQ ID NO 15
<211> LENGTH: 47
<212> TYPE: DNA
<213> ORGANISM: Artificial Sequence
<220> FEATURE:
<223> OTHER INFORMATION: synthetic DNA

<400> SEQUENCE: 15
atcgaggatc tcaatgatg atgatgatga tgggccggga tggcggc                     47

<210> SEQ ID NO 16
<211> LENGTH: 30
<212> TYPE: DNA
<213> ORGANISM: Artificial Sequence
<220> FEATURE:
<223> OTHER INFORMATION: synthetic DNA

<400> SEQUENCE: 16
atcgaggatc cattcggctt ttagggtagc                                       30

<210> SEQ ID NO 17
<211> LENGTH: 28
<212> TYPE: DNA
<213> ORGANISM: Artificial Sequence
<220> FEATURE:
<223> OTHER INFORMATION: synthetic DNA

<400> SEQUENCE: 17
tagctgagct catgggacag atctgagc                                         28

<210> SEQ ID NO 18
<211> LENGTH: 10
<212> TYPE: PRT
<213> ORGANISM: Gluconobacter oxydans

<400> SEQUENCE: 18

Met Ile Thr Arg Glu Thr Leu Lys Ser Leu
```

```
<210> SEQ ID NO 19
<211> LENGTH: 33
<212> TYPE: DNA
<213> ORGANISM: Artificial Sequence
<220> FEATURE:
<223> OTHER INFORMATION: synthetic DNA

<400> SEQUENCE: 19
taggaatatt tctcatgatt acgcgcgaaa ccc                           33

<210> SEQ ID NO 20
<211> LENGTH: 16
<212> TYPE: DNA
<213> ORGANISM: Artificial Sequence
<220> FEATURE:
<223> OTHER INFORMATION: synthetic DNA

<400> SEQUENCE: 20
gatgcttcag cacggc                                              16
```